US011311521B2

(12) United States Patent
Golden et al.

(10) Patent No.: US 11,311,521 B2
(45) Date of Patent: *Apr. 26, 2022

(54) SOLID DISPERSION FORMS OF RIFAXIMIN

(71) Applicant: Salix Pharmaceuticals, Inc., Bridgewater, NJ (US)

(72) Inventors: Pam Golden, Durham, NC (US); Mohammed A. Kabir, Cary, NC (US)

(73) Assignee: Salix Pharmaceuticals, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/468,457

(22) Filed: Sep. 7, 2021

(65) Prior Publication Data

US 2021/0401813 A1 Dec. 30, 2021

Related U.S. Application Data

(63) Continuation of application No. 17/174,829, filed on Feb. 12, 2021, now Pat. No. 11,129,817, which is a continuation of application No. 17/101,609, filed on Nov. 23, 2020, now abandoned, which is a continuation of application No. 16/369,509, filed on Mar. 29, 2019, now Pat. No. 10,874,647, which is a continuation of application No. PCT/US2017/054288, filed on Sep. 29, 2017.

(60) Provisional application No. 62/402,119, filed on Sep. 30, 2016.

(51) Int. Cl.
| | |
|---|---|
| *A61K 31/437* | (2006.01) |
| *A61K 9/28* | (2006.01) |
| *A61K 9/00* | (2006.01) |
| *A61P 1/16* | (2006.01) |
| *A61K 9/10* | (2006.01) |
| *A61K 47/02* | (2006.01) |
| *A61K 47/10* | (2017.01) |
| *A61K 47/12* | (2006.01) |
| *A61K 47/38* | (2006.01) |

(52) U.S. Cl.
CPC ............. *A61K 31/437* (2013.01); *A61K 9/00* (2013.01); *A61K 9/10* (2013.01); *A61K 9/2853* (2013.01); *A61K 9/2866* (2013.01); *A61K 47/02* (2013.01); *A61K 47/10* (2013.01); *A61K 47/12* (2013.01); *A61K 47/38* (2013.01); *A61P 1/16* (2018.01)

(58) Field of Classification Search
CPC ............................. A61K 31/437; A61P 1/16
See application file for complete search history.

(56) References Cited

U.S. PATENT DOCUMENTS

| | | |
|---|---|---|
| 4,341,785 A | 7/1982 | Marchi et al. |
| 4,557,866 A | 12/1985 | Cannata et al. |
| 6,352,720 B1 | 3/2002 | Martin et al. |
| 7,045,620 B2 | 5/2006 | Viscomi et al. |
| 7,612,199 B2 | 11/2009 | Viscomi et al. |
| 7,902,206 B2 | 3/2011 | Viscomi et al. |
| 7,906,542 B2 | 3/2011 | Viscomi et al. |
| 7,915,275 B2 | 3/2011 | Viscomi et al. |
| 7,928,115 B2 | 4/2011 | Forbes et al. |
| 8,158,644 B2 | 4/2012 | Viscomi et al. |
| 8,158,781 B2 | 4/2012 | Viscomi et al. |
| 8,193,196 B2 | 6/2012 | Viscomi et al. |
| 8,518,949 B2 | 8/2013 | Viscomi et al. |
| 8,568,782 B2 | 10/2013 | Viscomi et al. |
| 8,617,598 B2 | 12/2013 | Haeberlin et al. |
| 8,741,904 B2 | 6/2014 | Viscomi et al. |
| 8,835,452 B2 | 9/2014 | Viscomi et al. |
| 8,853,231 B2 | 10/2014 | Viscomi et al. |
| 9,271,968 B2 | 3/2016 | Viscomi et al. |
| 9,737,610 B2 | 8/2017 | Selbo et al. |
| 10,874,647 B2 | 12/2020 | Golden et al. |
| 11,129,817 B2 * | 9/2021 | Golden ............... A61K 9/2866 |
| 2004/0138231 A1 | 7/2004 | Bateman et al. |
| 2005/0101598 A1 | 5/2005 | Viscomi et al. |
| 2007/0141143 A1 | 6/2007 | Smithey et al. |
| 2007/0218138 A1 | 9/2007 | Bittorf et al. |
| 2008/0095754 A1 | 4/2008 | Burke et al. |
| 2009/0011020 A1 | 1/2009 | Viscomi et al. |
| 2009/0011024 A1 | 1/2009 | Babcock et al. |
| 2009/0028940 A1 | 1/2009 | Jahagirdar et al. |
| 2010/0174064 A1 | 7/2010 | Gushurst et al. |
| 2011/0312973 A1 | 12/2011 | Liepold et al. |
| 2012/0077835 A1 | 3/2012 | Selbo et al. |
| 2012/0214833 A1 | 8/2012 | Kulkarni et al. |
| 2017/0087134 A1 | 3/2017 | Golden et al. |
| 2017/0333562 A1 | 11/2017 | Selbo et al. |
| 2020/0397904 A1 | 12/2020 | Selbo et al. |

(Continued)

FOREIGN PATENT DOCUMENTS

| | | |
|---|---|---|
| AU | 2014202520 A1 | 5/2014 |
| CN | 103340856 A | 10/2013 |
| EP | 2011486 A1 | 1/2009 |

(Continued)

OTHER PUBLICATIONS

Bacchi et al., Polymorphism-structure relationships of rifamexil, an antibiotic rifamycin derivative. Mol Pharmacol. 1995;47(3):611-623.

Bajaj, Review article: potential mechanisms of action of rifaximin in the management of hepatic encephalopathy and other complications of cirrhosis. Aliment Pharmacol Ther. Jan. 2016;43 Suppl 1:11-26.

Bavin, Polymorphism in Process Development. Chemistry & Industry. Aug. 21, 1989;16:527-529.

Boulware, Travel medicine for the extreme traveler. Dis Mon. 2006;52(8):309-325.

Buhler, Polyvinylpyrrolidone Excipients for Pharmaceuticals, Povidone, Crospovidone and Copovidone. Springer, Chapter 2, Section 2.4.3, pp. 83-98, 2005.

Byrn et al., Hydrates and Solvates. Solid-State Chemistry of Drugs, Second Edition. SSCI, Inc., Chapter 11, pp. 233-247, (1999).

(Continued)

*Primary Examiner* — Kevin E Weddington
(74) *Attorney, Agent, or Firm* — McCarter & English, LLP; Michael J. DeGrazia

(57) ABSTRACT

Provided herein are solid dispersions comprising rifaximin and pharmaceutical compositions and uses thereof.

6 Claims, 4 Drawing Sheets

(56) References Cited

U.S. PATENT DOCUMENTS

2021/0205279 A1 7/2021 Golden et al.
2022/0040157 A1 2/2022 Golden et al.

FOREIGN PATENT DOCUMENTS

| EP | 2542225 A2 | 1/2013 |
|---|---|---|
| MX | 2012004954 A | 9/2012 |
| NZ | 231622 A | 5/1991 |
| WO | 2002/051385 A1 | 7/2002 |
| WO | 2006/026500 A1 | 3/2006 |
| WO | 2006/094737 A2 | 9/2006 |
| WO | 2009/108730 A2 | 9/2009 |
| WO | 2009/118167 A1 | 10/2009 |
| WO | 2010/040020 A1 | 4/2010 |
| WO | 2010/067072 A1 | 6/2010 |
| WO | 2011/051971 A2 | 5/2011 |
| WO | 2011/061748 A1 | 5/2011 |
| WO | 2012/009387 A1 | 1/2012 |
| WO | 2012/009388 A1 | 1/2012 |

OTHER PUBLICATIONS

Byrn et al., Pharmaceutical solids: a strategic approach to regulatory considerations. Pharm Res. 1995;12(7):945-954.

Castelli et al., Epidemiology of travelers' diarrhea. J Travel Med. 2001;8(Suppl 2):S26-S30.

Cheng et al., Update on Traveler's Diarrhea. Curr Infect Dis Rep. 2002;4(1):70-77.

ClinicalTrials.gov, Rifaximin Versus Placebo in the Prevention of Travelers' Diarrhea. Identifier: NCT00098384, 6 pages, May 9, 2006.

ClinicalTrials.gov, Rifaximin, Loperamide and the Combination to Treat Travelers' Diarrhea. Identifier: NCT00292344, 6 pages, Apr. 20, 2009.

Crum et al., New issues in infectious diarrhea. Rev Gastroenterol Disord. 2005;5 Suppl 3:S16-S25.

Datta et al., Crystal structures of drugs: advances in determination, prediction and engineering. Nat Rev Drug Discov. 2004;3(1):42-57.

Dupont et al., A randomized, double-blind, placebo-controlled trial of rifaximin to prevent travelers' diarrhea. Ann Intern Med. 2005;142(10):805-812.

Dupont et al., Rifaximin versus ciprofloxacin for the treatment of traveler's diarrhea: a randomized, double-blind clinical trial. Clin Infect Dis. 2001;33(11):1807-1815.

Dupont et al., Treatment of travelers' diarrhea: randomized trial comparing rifaximin, rifaximin plus loperamide, and loperamide alone. Clin Gastroenterol Hepatol. 2007;5(4):451-456.

Dupont, Treatment of travelers' diarrhea. J Travel Med. 2001;8(Suppl 2):S31-S33.

Emea, ICH Topic Q 6 A, Specifications: Test Procedures and Acceptance Criteria for New Drug Substances and New Drug Products: Chemical Substances. European Medicines Agency, CPMP/ICH/367/96. 32 pages, May 2000.

Ericsson, Rifaximin: a new approach to the treatment of travelers' diarrhea. Introduction. J Travel Med. 2001;8 (Suppl 2):S25-S26.

Evonik Industries, EUDRAGIT® Acrylic Drug Delivery Polymers. Retrieved online at: http://eudragit.evonik.com/product/eudragit/en/products-services/eudragit-products/pages/default.aspx>> published on Apr. 23, 2010 as per Wayback Machine. 1 page.

FDA, Guideline for Submitting Supporting Documentation in Drug Applications for the Manufacture of Drug Substances. Center for Drug Evaluation and Research, Food and Drug Administration, Department of Health and Human Services. 47 pages, Feb. 1987.

Fiorucci et al., Inhibition of intestinal bacterial translocation with rifaximin modulates lamina propria monocytic cells reactivity and protects against inflammation in a rodent model of colitis. Digestion. 2002;66(4):246-256.

Gerard et al., Rifaximin: a nonabsorbable rifamycin antibiotic for use in nonsystemic gastrointestinal infections. Expert Rev Anti Infect Ther. 2005;3(2):201-211.

Ghoshal et al., Models for prediction of mortality from cirrhosis with special reference to artificial neural network: a critical review. Hepatol Int. 2008;2(1):31-38.

Gillis et al., Rifaximin. A review of its antibacterial activity, pharmacokinetic properties and therapeutic potential in conditions mediated by gastrointestinal bacteria. Drugs. 1995;49(3):467-484.

Gionchetti et al., Rifaximin in patients with moderate or severe ulcerative colitis refractory to steroid-treatment: a double-blind, placebo-controlled trial. Dig Dis Sci. 1999;44(6):1220-1221.

Guillory, Generation of Polymorphs, Hydrates, Solvates, and Amorphous Solids. Materials Science. Chapter 5, pp. 183-226, (1999).

Hancock et al., Characteristics and significance of the amorphous state in pharmaceutical systems. J Pharm Sci. Jan. 1997;86(1):1-12.

Huang et al., Rifaximin—a novel antimicrobial for enteric infections. J Infect. 2005;50(2):97-106.

Infante et al., Enteroaggregative *Escherichia coli* diarrhea in travelers: response to rifaximin therapy. Clin Gastroenterol Hepatol. 2004;2(2):135-138.

Jozwiakowski, Alteration of the Solid State of the Drug Substance: Polymorphs, Solvates, and Amorphous Forms. Water-Insoluble Drug Formulation. Ron Liu (Ed.), Taylor & Francis Group. Chapter 15, pp. 525-568, (2000).

Khankari et al., Pharmaceutical hydrates. Thermochimica Acta. 1995;248:61-79.

Koo et al., Current and future developments in travelers' diarrhea therapy. Expert Rev Anti Infect Ther. 2006;4(3):417-427.

Koo et al., The role of rifaximin in the treatment and chemoprophylaxis of travelers' diarrhea. Ther Clin Risk Manag. 2009;5:841-848.

Leuner et al., Improve Drug Solubility for Oral Delivery using Solid Dispersions. European Journal of Pharmaceutics and Biopharmaceutics. 2000;50:47-60.

Malamud et al., Treatment of gastrointestinal infections. Curr Opin Gastroenterol. 2000;16(1):51-55.

Martins, et al., Microstructured Ternary Solid Dispersions to Improve Carbamazepine Solubility. Powder Technology. Jan. 2012;215-216:156-165.

Mas et al., Comparison of rifaximin and lactitol in the treatment of acute hepatic encephalopathy: results of a randomized, double-blind, double-dummy, controlled clinical trial. J Hepatol. 2003;38(1):51-58.

Miglioli et al., Effects of daily oral administration of rifaximin and neomycin on faecal aerobic flora in rats. Pharmacol Res. 2001;44(5):373-375.

Neff et al., Analysis of hospitalizations comparing rifaximin versus lactulose in the management of hepatic encephalopathy. Transplant Proc. 2006;38(10):3552-3555.

Newman et al., Form Selection of Pharmaceutical Compounds. Handbook of Pharmaceutical Analysis. Lena Ohannesian (Ed.), Marcel Dekker, Inc., New York. Chapter 1, 61 pages, (2002).

Paik et al., Comparison of rifaximin and lactulose for the treatment of hepatic encephalopathy: a prospective randomized study. Yonsei Med J. 2005;46(3):399-407.

Pakyz, Rifaximin: a new treatment for travelers' diarrhea. Ann Pharmacother. 2005;39(2):284-289.

Pawlowski et al., Diagnosis and treatment of acute or persistent diarrhea. Gastroenterology. 2009;136(6):1874-1886.

Pelizza et al., Polymorphism of rifampicin. Farmaco Sci. 1977;32(7):471-481.

Pigott, Foodborne illness. Emerg Med Clin North Am. 2008;26(2):475-497.

Preidis et al., Targeting the human microbiome with antibiotics, probiotics, and prebiotics: gastroenterology enters the metagenomics era. Gastroenterology. 2009;136(6):2015-2031.

Scarpignato et al., Prevention and treatment of traveler's diarrhea: a clinical pharmacological approach. Chemotherapy. 1995;41 Suppl 1:48-81.

Scarpignato et al., Rifaximin, a poorly absorbed antibiotic: pharmacology and clinical potential. Chemotherapy. 2005;51 Suppl 1:36-66.

Steffen et al., Therapy of travelers' diarrhea with rifaximin on various continents. Am J Gastroenterol. 2003;98(5):1073-1078.

(56) References Cited

OTHER PUBLICATIONS

Steffen, Rifaximin: a nonabsorbed antimicrobial as a new tool for treatment of travelers' diarrhea. J Travel Med. 2001;8(Suppl 2):S34-S39.

Su et al., Utility of the Nonabsorbed (<0.4%) Antibiotic Rifaximin in Gastroenterology and Hepatology. Gastroenterol Hepatol (N Y). 2006;2(3):186-197.

Taylor et al., A randomized, double-blind, multicenter study of rifaximin compared with placebo and with ciprofloxacin in the treatment of travelers' diarrhea. Am J Trop Med Hyg. 2006;74(6):1060-1066.

Taylor et al., Systemic pharmacokinetics of rifaximin in volunteers with shigellosis. Antimicrob Agents Chemother. 2008;52(3):1179-1181.

Trinh et al., Diarrheal diseases in the elderly. Clin Geriatr Med. 2007;23(4):833-856.

Van Den Mooter, Solid Dispersions as a Formulation Strategy for Poorly Soluble Compounds. 20th Annual Symposium of the Finish Society of Physical Pharmacy; Vithi, Finland; Katholieke Universiteit Leuven; 37 pages; Jan. 28-29, 2009.

Vasconcelos et al., Solid dispersions as strategy to improve oral bioavailability of poor water soluble drugs. Drug Discov Today. Dec. 2007;12(23-24):1068-75.

Vippagunta et al., Crystalline solids. Adv Drug Deliv Rev. 2001;48(1):3-26.

Visser et al., Inulin solid dispersion technology to improve the absorption of the BCS Class IV drug TMC240. Eur J Pharm Biopharm. Feb. 2010;74(2):233-8.

Vlachogiannakos et al., Long-term administration of rifaximin improves the prognosis of patients with decompensated alcoholic cirrhosis. J Gastroenterol Hepatol. Mar. 2013;28(3):450-5.

Williams et al., Rifaximin, a nonabsorbed oral antibiotic, in the treatment of hepatic encephalopathy: antimicrobial activity, efficacy, and safety. Rev Gastroenterol Disord. 2005;5 Suppl 1:S10-S18.

Xifaxan (rifaximin) Tablets, NDA21-361/S-006. www.salix.com, 16 pages, (2006).

Xifaxan (rifaximin) Tablets, Revised Xifaxan Label, www.salix.com, 13 pages, May 21, 2004.

Declaration Under 37 C.F. R. Sec. 1.132 for U.S. Appl. No. 10/728,090. Polymorph forms of rifaximin, processes for their production and use thereof in medicinal preparations. Viscomi. 12 pages, Jan. 10, 2006.

U.S. Appl. No. 15/281,543, filed Sep. 30, 2016, 2017-0087134, Published.

U.S. Appl. No. 17/174,829, filed Feb. 12, 2021, 2021-0205279, Published.

Kalambokis et al., Rifaximin for the prevention of spontaneous bacterial peritonitis. World J Gastroenterol. Apr. 14, 2012;18(14):1700-1702.

U.S. Appl. No. 13/181,481, filed Jul. 12, 2011, 2012-0077835, Abandoned.

U.S. Appl. No. 14/250,293, filed Apr. 10, 2014, U.S. Pat. No. 9,737,610, Issued.

U.S. Appl. No. 15/281,543, filed Sep. 30, 2016, 2017-0087134, Abandoned.

U.S. Appl. No. 15/615,121, filed Jun. 6, 2017, 2017-0333562, Abandoned.

U.S. Appl. No. 16/916,421, filed Jun. 30, 2020, 2020-0397904, Published.

U.S. Appl. No. 16/369,509, filed Mar. 29, 2019, U.S. Pat. No. 10,874,647, Issued.

U.S. Appl. No. 17/101,609, filed Nov. 23, 2020, Abandoned.

U.S. Appl. No. 17/174,829, filed Feb. 12, 2021, U.S. Pat. No. 11,129,817, Issued.

U.S. Appl. No. 17/468,461, filed Sep. 7, 2021, 2022-0040157, Published.

\* cited by examiner

SOLID DISPERSION FORMS OF RIFAXIMIN

RELATED APPLICATIONS

This application is a continuation of U.S. patent application Ser. No. 17/174,829, filed Feb. 12, 2021, which is a continuation of U.S. patent application Ser. No. 17/101,609, filed Nov. 23, 2020, which is a continuation of U.S. patent application Ser. No. 16/369,509, now U.S. Pat. No. 10,874,647, filed Mar. 29, 2019, which is a continuation of International Patent Application No. PCT/US2017/054288, filed Sep. 29, 2017 which claims priority to U.S. Provisional Application No. 62/402,119, filed Sep. 30, 2016, the entire contents of each of which are incorporated herein by reference.

BACKGROUND

The incidence of liver disease is on the rise and will continue to be a major health burden. Cirrhosis is a major cause of much of the chronic liver disease (CLD) in at least the U.S., and is the 12th leading cause of death. Mortality rates from complications of cirrhosis using data from the Nationwide Inpatient Sample (NIS) database from 1998 to 2006 were estimated to be approximately 8%, 18%, 10%, and 45% for ascites, hepatic encephalopathy (HE), variceal bleeding, and hepatorenal syndrome (HRS), respectively. See e.g., Mol Pharm. 2011; 8:1573-1581. Similarly, other studies have demonstrated that the in-hospital mortality of patients with spontaneous bacterial peritonitis (SBP) ranges from 10-50%. See e.g., Hepatology, 1993 February; 17(2): 251-7; J Hepatol, 2004 May; 40(5):823-30.

The management of cirrhosis and its complications is based on disease severity and whether or not complications have developed (i.e., decompensated disease). The development of esophageal variceal bleeding (EVB), ascites, spontaneous bacterial peritonitis (SBP), HE or hepatorenal syndrome (HRS) has a profound impact on prognosis. Despite current medical therapies for EVB, ascites, SBP, and HE, patients with compensated disease who develop one of these complications have a five-year survival rate of 20% to 50% (Gastroenterology 1987; 93: 234-241; Gastroenterology. 1997; 112:463-472). The survival rate of patients who develop SBP or HRS is particularly poor. For SBP, less than half will survive 1-year; the median survival rate for patients with type I HRS is less than 2 weeks (Gastroenterology. 1993; 104:1133-8: Gastroenterology 1993; 105: 229-236).

The use of rifaximin in preventing complications of cirrhosis is supported by multiple lines of clinical and experimental evidence. For example, rifaximin was approved by the US FDA in March 2010 for the reduction in risk of recurrent overt HE; is shown to protect from HE recurrences with decreased HE-related and all-cause hospitalizations without an increased rate of adverse events (AEs) or decreased survival (see e.g., Conf. Proc. IEEE Eng. Med. Biol. Soc. 2013 2184-2187); reduces or maintains the overall rates of infection, antibiotic use, and other complications of cirrhosis such as ascites (see Conf. Proc. IEEE Eng. Med. Biol. Soc. supra); and was independently associated with higher survival and lower risk of developing variceal bleeding, HE, SBP, or HRS (see e.g., Journal of Gastroenterology and Hepatology 28(3); December 2012).

Given the therapeutic value of rifaximin, and the continued escalation of liver disease, alternative formulations, the discovery of alternative formulations and uses of rifaximin remains.

SUMMARY

It has now been discovered that certain pharmaceutical compositions comprising solid dispersions of rifaximin effectively reduce the time to hospitalization and prevent all-cause mortality associated with complications of liver disease. See e.g., FIG. 3 and FIG. 4.

It has also been discovered that certain pharmaceutical compositions comprising solid dispersions of rifaximin reduce the time to development of refractory ascites. See e.g., Table 43.

The present disclosure provides these pharmaceutical compositions as well as methods for their manufacture, and therapeutic uses associated with complications of liver disease.

DETAILED DESCRIPTION

Figure 1:
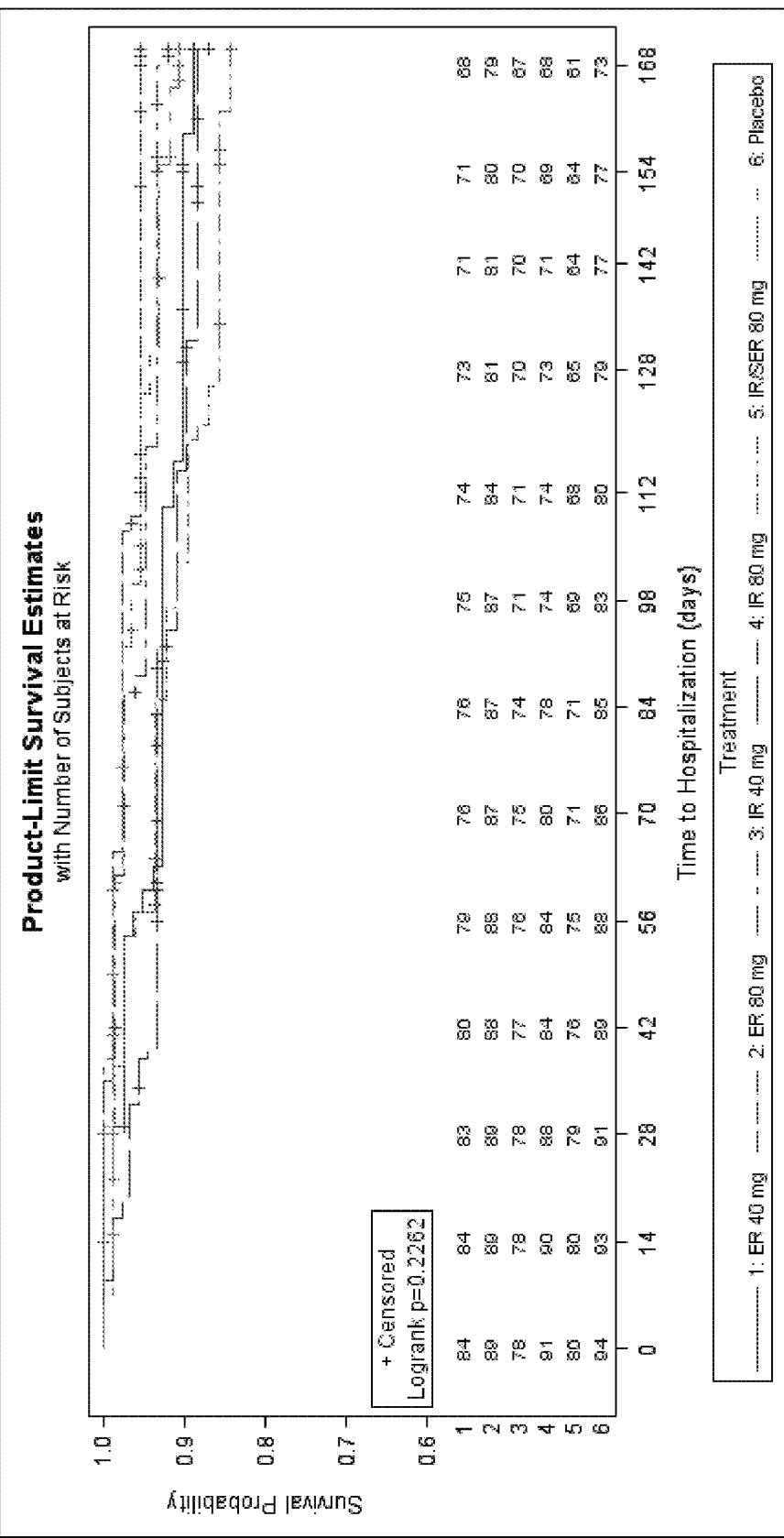
FIG. 1 presents a Kaplan-Meier estimate for the distribution of time to hospitalization for any of the liver cirrhosis complications by treatment group for an ITT (intent-to-treat) population with a formulation comprising rifaximin solid dispersion.

Provided herein are solid dispersions comprising rifaximin and hydroxypropyl methylcellulose acetate succinate (HPMC-AS).

Definitions

The term "solid dispersion" or as used herein refers to a dispersion of rifaximin and an inert carrier matrix in a solid form, i.e., rifaximin is homologously mixed with an inert carrier. The inert matrix is generally hydrophilic (e.g., a polymer such as HPMC-AS) and may be crystalline or amorphous. It will be understood that it is not necessarily the preparation method that governs the properties of the solid dispersion, but rather the molecular arrangement of the contents of the dispersion. Thus, absent an expression to do so, or an incorporation of process restrictions, solid dispersions are not to be limited by the process to which they are made. The terms "solid dispersion", "soluble solid dispersion", and the abbreviations "SD" or "SDD" are used interchangeably and each refer to the disclosed solid dispersion of rifaximin.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The language "therapeutically effective amount" refers to an amount of a composition comprising a solid dispersion of rifaximin effective, upon single or multiple dose administration to the subject to provide a therapeutic benefit to the subject.

"Hepatic encephalopathy" or "HE" for shorthand is defined as an altered mental status diagnosed as HE and defined as an increase of the Conn score to Grade ≥2 (i.e., 0 or 1 to ≥2).

"Esophageal variceal bleeding" or "EVB" for shorthand is defined as the occurrence of a clinically significant gastrointestinal bleed being defined as 1) bleeding from an esophageal or gastric varix at the time of endoscopy or 2) the presence of large varices with blood evident in the stomach, and no other identifiable cause of bleeding observed during endoscopy, and at least one or more of the following criteria is present: i) drop in hemoglobin of greater than 2 g/dL over the first 48 hours post hospital admission, ii) transfusion requirement of 2 units of blood or more within 24 hours of hospital admission, iii) a systolic blood pressure of less than 100 mm Hg, or iv) pulse rate greater than 100 beat/min at the time of admission.

"Spontaneous bacterial peritonitis or "SBP" for shorthand is defined as greater than 250 polymorphonuclear (PMN) cells/mm$^3$ and/or positive monomicrobial culture in the ascitic fluid.

"Hepatorenal syndrome" (HRS) is defined as i) progressive rise in serum creatinine (>1.5 mg/dL) with no improvement after at least 2 days with diuretic withdrawal and volume expansion with albumin, ii) absence of parenchymal kidney disease, iii) oliguria, iv) absence of shock, and v) no current or recent (within 3 months prior randomization) treatment with nephrotoxic drugs.

"Time to development of medically refractory ascites" is defined as ascites which can either no longer be effectively managed by i) a low sodium diet and maximal doses of diuretics (e.g., up to 400 mg spironolactone and 160 mg furosemide per day) or ii) diuretics, due to the inability to tolerate side effects of maximal doses of diuretics.

In the present disclosure, when a numerical value is modified by the term "about", the exact numerical value is also deemed to be disclosed.

Compositions

In a first embodiment, the present disclosure provides a solid dispersion comprising rifaximin and HPMC-AS.

In a second embodiment, the present disclosure provides a solid dispersion comprising rifaximin and HPMC-AS, wherein the HPMC-AS is present in an amount of from about 10 wt % to about 60 wt %, from about 10 wt % to about 50 wt %, from about 10 wt % to about 40 wt % from about 12 wt % to about 38 wt %, from about 15 wt % to about 35 wt %, from about 16 wt % to about 34 wt %, from about 30 wt % to about 40 wt %, from about 30 wt % to about 35 wt %, from about 33 wt % to about 35 wt %, about 32 wt %, about 33 wt %, about 34 wt %, about 35 wt %, from about 10 wt % to about 20 wt %, from about 13 wt % to about 18 wt %, from about 16 wt % to about 18 wt %, about 15 wt %, about 16 wt %, about 17 wt %, about 18 wt %, from about 40 wt % to about 50 wt %, from about 46 wt % to about 49 wt %, about 46 wt %, about 47 wt %, or about 48 wt %. In one alternative, the amount of HPMC-AS present in the solid dispersion is about 46 wt % to about 49 wt %, about 46 wt %, about 47 wt %, about 48 wt %, from about 33 wt % to about 35 wt %, about 33 wt %, about 34 wt %, about 35 wt %, from about 16 wt % to about 34 wt %, from about 16 wt % to about 18 wt %, about 16 wt %, about 17 wt %, or about 18 wt %. In another alternative, the amount of HPMC-AS present in the solid dispersion is about 46 wt %, about 47 wt %, about 48 wt %, about 33 wt %, about 34 wt %, about 35 wt %, about 16 wt %, about 17 wt %, or about 18 wt % HPMC-AS. In yet another alternative, the amount of HPMC-AS present in the solid dispersion is about 46 wt %, about 47 wt %, or about 48 wt %.

In a third embodiment, the solid dispersion comprises equal amounts of rifaximin and polymer. Thus, for example, the solid dispersion comprises from about 10 wt % to about 60 wt %, from about 10 wt % to about 50 wt %, from about 10 wt % to about 40 wt %, from about 12 wt % to about 38 wt %, from about 15 wt % to about 35 wt %, from about 16 wt % to about 34 wt %, from about 30 wt % to about 40 wt %, from about 30 wt % to about 35 wt %, from about 33 wt % to about 35 wt %, about 32 wt %, about 33 wt %, about 34 wt %, about 35 wt %, from about 10 wt % to about 20 wt %, from about 13 wt % to about 18 wt %, from about 16 wt % to about 18 wt %, about 15 wt %, about 16 wt %, about 17 wt %, about 18 wt %, from about 40 wt % to about 50 wt %, from about 46 wt % to about 49 wt %, about 46 wt %, about 47 wt %, or about 48 wt % rifaximin and HPMC-AS. In another aspect, the solid dispersion comprises from about 46 wt % to about 49 wt %, about 46 wt %, about 47 wt %, about 48 wt %, from about 33 wt % to about 35 wt %, about 33 wt %, about 34 wt %, about 35 wt %, from about 16 wt % to about 34 wt %, from about 16 wt % to about 18 wt %, about 16 wt %, about 17 wt %, or about 18 wt % rifaximin and HMPC-AS. In another aspect, the solid dispersion comprises about 46 wt %, about 47 wt %, about 48 wt %, about 33 wt %, about 34 wt %, about 35 wt %, about 16 wt %, about 17 wt %, or about 18 wt % rifaximin and HPMC-AS. In yet another aspect, the solid dispersion comprises about 46 wt %, about 47 wt %, or about 48 wt % rifaximin and HPMC-AS.

In a fourth embodiment, the solid dispersion comprising rifaximin and HPMC-AS further comprises poloxamer 407 (e.g., Pluronic® F-127), wherein the remaining components and amounts present in the solid dispersion are as described in the second or third embodiment.

In a fifth embodiment, the solid dispersion comprising rifaximin and HPMC-AS further comprises poloxamer 407 (e.g., Pluronic® F-127) in an amount from about 0.5 wt % to about 7 wt %, from about 0.5 wt % to about 5 wt %, from about 1 wt % to about 5 wt %, from about 1 wt % to about 4 wt %, from about 2 wt % to about 4 wt %, from about 4 wt % to about 6 wt %, from about 3 wt % to about 5 wt %, from about 2 wt % to about 4 wt %, from about 1 wt % to about 2 wt %, about 1 wt %, about 2 wt %, about 3 wt %, about 4 wt %, about 5 wt %, about 5.5 wt %, or about 6 wt %, wherein the remaining components and amounts present in the solid dispersion are as described in the second, third, or fourth embodiment. In one alternative, the solid dispersion comprises about 1 wt %, about 2 wt %, about 3 wt %, about 4 wt %, about 5 wt %, about 5.5 wt %, about 5.6 wt %, about 5.7 wt %, or about 6 wt % poloxamer 407 (e.g., Pluronic® F-127), wherein the remaining components and amounts present in the solid dispersion are as described in the second, third, or fourth embodiment. In yet another alternative, the solid dispersion of rifaximin comprises about 5 wt %, about 5.5 wt %, or about 6 wt % poloxamer 407 (e.g., Pluronic® F-127), wherein the remaining components and amounts present in the solid dispersion are as described in the second, third, or fourth embodiment.

In a sixth embodiment, provided are pharmaceutical compositions comprising the solid dispersion of any one of the first, second, third, fourth, or fifth embodiment.

In a seventh embodiment, provided are pharmaceutical compositions comprising the solid dispersions of any one of the first, second, third, fourth, or fifth embodiments together with croscarmellose sodium (crosslinked carboxymethyl cellulose sodium).

In an eighth embodiment, provided are pharmaceutical compositions comprising the solid dispersions of any one of the first, second, third, fourth, or fifth embodiments together with croscarmellose sodium in an amount from about 2 wt % to about 15 wt %, from about 3 wt % to about 14 wt %, from about 4 wt % to about 14 wt %, from about 2 wt % to about 13 wt %, from about 3 wt % to about 13 wt %, from about 4 wt % to about 13 wt %, from about 11 wt % to about 14 wt %, from about 12 wt % to about 14 wt %, from about 4 wt % to about 10 wt %, about 12 wt %, about 12.5 wt %, about 13 wt %, about 13.5 wt %, from about 4 wt % to about 6 wt %, about 5 wt %, from about 8% to about 10 wt %, or about 9 wt % based on the total amount (wt %) of components in the pharmaceutical composition, wherein the remaining components and amounts present in the pharmaceutical composition include and are as described in the second, third, fourth, fifth, sixth, or seventh embodiment. In one alternative, the croscarmellose sodium is present in an amount from about 4 wt % to about 14 wt %, from about 12 wt % to about 14 wt %, about 13 wt %, from about 4 wt % to about 6 wt %, about 5 wt %, from about 8% to about 10 wt %, or about 9 wt % based on the total amount (wt %) of components in the pharmaceutical composition, wherein the remaining components and amounts present in the pharmaceutical composition include and are as described in the second, third, fourth, fifth, sixth, or seventh embodiment. In another alternative, the croscarmellose sodium is present in an amount from of rifaximin is about 13 wt %, about 5 wt %, or about 9 wt % based on the total amount (wt %) of components in the pharmaceutical composition, wherein the remaining components and amounts present in the pharmaceutical composition include and are as described in the second, third, fourth, fifth, sixth, or seventh embodiment.

In a ninth embodiment, the pharmaceutical compositions described herein further comprise microcrystalline cellulose, wherein the remaining components and amounts present in the pharmaceutical composition include and are as described in the second, third, fourth, fifth, sixth, seventh, or eighth embodiment.

In a tenth embodiment, the pharmaceutical compositions described herein further comprise microcrystalline cellulose present in an amount from about 5 wt % to about 60 wt %, from about 10 wt % to about 55 wt %, from about 5 wt % to about 15 wt %, from about 8 wt % to about 13 wt %, from about 10 wt % to about 12 wt %, from about 10 wt % to about 19 wt %, about 11 wt %, from about 15 wt % to about 25 wt %, from about 17 wt % to about 19 wt %, about 18 wt %, from about 40 wt % to about 60 wt %, from about 45 wt % to about 55 wt %, from about 49 wt % to about 55 wt %, from about 49 wt % to about 51 wt %, from about 53 wt % to about 55 wt %, about 50 wt %, or about 54 wt % based on the total amount (wt %) of components in the pharmaceutical composition, wherein the remaining components and amounts present in the pharmaceutical composition include and are as described in the second, third, fourth, fifth, sixth, seventh, eighth, or ninth embodiment.

In an eleventh embodiment, the pharmaceutical compositions described herein further comprise colloidal silicon dioxide, wherein the remaining components and amounts present in the pharmaceutical composition include and are as described in the second, third, fourth, fifth, sixth, seventh, eighth, ninth, or tenth embodiment.

In a twelfth embodiment, the pharmaceutical compositions described herein further comprise colloidal silicon dioxide present in an amount from about 0.1 wt % to about 0.3 wt %, from about 0.15 wt % to about 0.25 wt %, or about 0.2 wt % based on the total amount (wt %) of components in the pharmaceutical composition, wherein the remaining components and amounts present in the pharmaceutical composition include and are as described in the second, third, fourth, fifth, sixth, seventh, eighth, ninth, tenth, or eleventh embodiment.

In a thirteenth embodiment, the pharmaceutical compositions described herein further comprise magnesium stearate, wherein the remaining components and amounts present in the pharmaceutical composition include and are as described in the second, third, fourth, fifth, sixth, seventh, eighth, ninth, tenth, eleventh, or twelfth embodiment.

In a fourteenth embodiment, the pharmaceutical compositions described herein further comprise magnesium stearate present in an amount from about 0.3 wt % to about 0.6 wt %, from about 0.4 wt % to about 0.6 wt %, from about 0.45 wt % to about 0.55 wt %, about 0.45 wt %, about 0.47 wt %, or about 0.49 wt % based on the total amount (wt %) of components in the pharmaceutical composition, wherein the remaining components and amounts present in the pharmaceutical composition include and are as described in the second, third, fourth, fifth, sixth, seventh, eighth, ninth, tenth, eleventh, twelfth, or thirteenth embodiment.

In a fifteenth embodiment, provided is a provided is a pharmaceutical composition comprising from about 33 wt % to about 35 wt % rifaximin; from about 33 wt % to about 35 wt % HPMC-AS; from about 3 wt % to about 5 wt % poloxamer 407; from about 4 wt % to about 14 wt % croscarmellose sodium; from about 10 wt % to about 19 wt % microcrystalline cellulose; from about 0.15 wt % to about 0.25 wt % colloidal silicon dioxide; and from about 0.45 wt % to about 0.55 wt % magnesium stearate.

In a sixteenth embodiment, provided is a pharmaceutical composition according to the fifteenth embodiment, wherein comprising the croscarmellose sodium is present in an amount of from about 12 wt % to about 14 wt %. Alternatively, provided is a pharmaceutical composition according to the fifteenth embodiment, wherein comprising the croscarmellose sodium is present in an amount of about 13%.

In a seventeenth embodiment, provided is a pharmaceutical composition according to the fifteenth or sixteenth embodiment wherein the microcrystalline cellulose is present in an amount from about 10 wt % to about 12 wt %. Alternatively, provided is a pharmaceutical composition according to the fifteenth or sixteenth embodiment wherein the microcrystalline cellulose is present in an amount of about 11 wt %.

In an eighteenth embodiment, provided is a pharmaceutical composition according to the fifteenth embodiment, wherein the croscarmellose sodium is present in an amount from about 4 wt % to about 6 wt %. Alternatively, provided is a pharmaceutical composition according to the fifteenth embodiment, wherein the croscarmellose sodium is present in an amount of about 5 wt %.

In a nineteenth embodiment, provided is a pharmaceutical composition according to the fifteenth or eighteenth embodiment, wherein the microcrystalline cellulose is present in an amount from about 17 wt % to about 19 wt %. Alternatively, provided is a pharmaceutical composition according to the fifteenth or eighteenth embodiment, wherein the microcrystalline cellulose is present in an amount of about 18 wt %.

In a twentieth embodiment, provided is a pharmaceutical composition according to the fifteenth, sixteenth, seventeenth, eighteenth, or nineteenth embodiment, wherein the poloxamer 407 is present in an amount of about 4%.

In a twenty-first embodiment, provided is a pharmaceutical composition according to the fifteenth, sixteenth, seventeenth, eighteenth, nineteenth, or twentieth embodiment, wherein the colloidal silicon dioxide is present in an amount of about 0.20 wt %.

In a twenty-second embodiment, provided is a pharmaceutical composition according to the fifteenth, sixteenth, seventeenth, eighteenth, nineteenth, twentieth, or twenty-first embodiment, wherein the magnesium stearate is present in an amount of about 0.50 wt %.

In a twenty-third embodiment, provided is a pharmaceutical composition according to the fifteenth, sixteenth, seventeenth, eighteenth, nineteenth, twentieth, twenty-first, or twenty-second embodiment, wherein the rifaximin is present in an amount of about 34%.

In a twenty-fourth embodiment, provided is a pharmaceutical composition according to the fifteenth, sixteenth, seventeenth, eighteenth, nineteenth, twentieth, twenty-first, twenty-second, or twenty-third embodiment, wherein the HPMC-AS is present in an amount of about 34%.

In a twenty-fifth embodiment, provided is a pharmaceutical composition according to the fifteenth, sixteenth, seventeenth, eighteenth, nineteenth, twentieth, twenty-first, twenty-second, twenty-third embodiment, or twenty fourth embodiment, wherein the total amount of rifaximin is about 80 mg.

In a twenty-sixth embodiment, provided is a pharmaceutical composition comprising from about 16 wt % to about 18 wt % rifaximin; from about 16 wt % to about 18 wt % HPMC-AS; from about 1 wt % to about 2 wt % poloxamer 407; from about 4 wt % to about 10 wt % croscarmellose sodium; from about 49 wt % to about 55 wt % microcrystalline cellulose; from about 0.15 wt % to about 0.25 wt % colloidal silicon dioxide; and from about 0.45 wt % to about 0.55 wt % magnesium stearate.

In a twenty-seventh embodiment, provided is a pharmaceutical composition according to the twenty-sixth embodiment, wherein the croscarmellose sodium is present in an amount from about 8 wt % to about 10 wt %. Alternatively, provided is a pharmaceutical composition according to the twenty-sixth embodiment, wherein the croscarmellose sodium is present in an amount of about 9 wt %.

In a twenty-eighth embodiment, provided is a pharmaceutical composition according to the twenty-sixth or twenty-seventh embodiment, wherein the microcrystalline cellulose is present in an amount from about 49 wt % to about 51 wt %. Alternatively, provided is a pharmaceutical composition according to the twenty-sixth or twenty-seventh embodiment, wherein the microcrystalline cellulose is present in an amount of about 51 wt %.

In a twenty-ninth embodiment, provided is a pharmaceutical composition according to the twenty-sixth embodiment, wherein the croscarmellose sodium is present in an amount from about 4 wt % to about 6 wt %. Alternatively, provided is a pharmaceutical composition according to the twenty-sixth embodiment, wherein the croscarmellose sodium is present in an amount of about 5 wt %.

In a thirtieth embodiment, provided is a pharmaceutical composition according to the twenty-sixth or twenty-ninth embodiment, wherein the microcrystalline cellulose is present in an amount from about 53 wt % to about 55 wt %. Alternatively, provided is a pharmaceutical composition according to the twenty-sixth or twenty-ninth embodiment, wherein the microcrystalline cellulose is present in an amount of about 54 wt %.

In a thirty-first embodiment, provided is a pharmaceutical composition according to the twenty-sixth, twenty-seventh, twenty-eighth, twenty-ninth, or thirtieth embodiment, wherein colloidal silicon dioxide is present in an amount of about 0.20 wt %.

In a thirty-second embodiment, provided is a pharmaceutical composition according to the twenty-sixth, twenty-seventh, twenty-eighth, twenty-ninth, thirtieth, or thirty-first embodiment, wherein the magnesium stearate is present in an amount of about 0.50 wt %.

In a thirty-third embodiment, provided is a pharmaceutical composition according to the twenty-sixth, twenty-seventh, twenty-eighth, twenty-ninth, thirtieth, thirty-first, or thirty-second embodiment, wherein the rifaximin is present in an amount of about 17 wt %.

In a thirty-fourth embodiment, provided is a pharmaceutical composition according to the twenty-sixth, twenty-seventh, twenty-eighth, twenty-ninth, thirtieth, thirty-first, thirty-second, or thirty-third embodiment, wherein the HMPC-AS is present in an amount of about 17 wt %.

In a thirty-fifth embodiment, provided is a pharmaceutical composition according to the twenty-sixth, twenty-seventh, twenty-eighth, twenty-ninth, thirtieth, thirty-first, thirty-second, thirty-third, or thirty-fourth embodiment, wherein the total amount of rifaximin is 40 mg.

In a thirty-sixth embodiment, the pharmaceutical compositions described herein are in the form of a tablet.

In a thirty-seventh embodiment, the pharmaceutical compositions described herein are in the form of a tablet, and are immediate release or sustained extended release. In one alternative, the pharmaceutical composition is a sustained extended release tablet.

In a thirty-eighth embodiment, the pharmaceutical compositions described herein are film coated. Coatings are known to those of skill in the art and may immediate release or sustained release coatings. An example of a film coating is Opadry II Blue 85F90614 by Colorcon®.

Other solid dispersions and pharmaceutical compositions included in the present disclosure are described in the Exemplification section below.

Uses, Formulation and Administration Dosage Forms

According to other embodiments, the present disclosure relates to a method of using the disclosed solid dispersions pharmaceutical compositions thereof to prevent complications of liver cirrhosis such as e.g., in subjects with early decompensation.

Also provided herein are methods of using the solid dispersions and pharmaceutical compositions thereof to prevent all-cause mortality e.g., in subjects with liver cirrhosis who may also have early decompensation.

Also provided herein are methods of using the solid dispersions and pharmaceutical compositions thereof to reduce the time to hospitalization that is associated with complications of liver disease (e.g., liver cirrhosis complications) such as e.g., reducing the time to hospitalization from one or more of hepatic encephalopathy (HE), esophageal variceal bleeding (EVB), spontaneous bacterial peritonitis (SBP), and hepatorenal syndrome (HRS).

Also provided herein are methods of using the solid dispersions and pharmaceutical compositions thereof to prevent hospitalization that is associated with complications of liver disease (e.g., liver cirrhosis complications) such as e.g., reducing the time to hospitalization from one or more of hepatic encephalopathy (HE), esophageal variceal bleeding (EVB), spontaneous bacterial peritonitis (SBP), and hepatorenal syndrome (HRS).

Also provided herein are methods of using the solid dispersions and pharmaceutical compositions thereof to reduce the time to all-cause mortality that is associated with complications of liver disease (e.g., liver cirrhosis complications) such as e.g., reducing the time to all-cause mortality from one or more of hepatic encephalopathy (HE), esophageal variceal bleeding (EVB), spontaneous bacterial peritonitis (SBP), and hepatorenal syndrome (HRS).

Also provided herein are methods of using the solid dispersions and pharmaceutical compositions thereof to prevent all-cause mortality that is associated with complications of liver disease (e.g., liver cirrhosis complications) such as e.g., reducing the time to all-cause mortality from one or more of hepatic encephalopathy (HE), esophageal variceal bleeding (EVB), spontaneous bacterial peritonitis (SBP), and hepatorenal syndrome (HRS).

Further provided are methods of using the solid dispersions and pharmaceutical compositions thereof to reduce the time to development of refractory ascites in e.g., subjects having early decompensated liver cirrhosis or liver cirrhosis complications such as HE, EVB, SBP, or HRS.

Suitable dosage forms that can be used with the solid dispersions and compositions herein include, but are not limited to, capsules, tablets, mini-tablets, beads, beadlets, pellets, granules, granulates, and powder. Suitable dosage forms may be coated, for example using an enteric coating. In some embodiments, the solid dispersions and compositions are formulated as tablets, caplets, or capsules. In one embodiment, the solid dispersions and compositions are formulated as a tablet.

Provided compositions may be formulated such that a dosage of between 0.001-100 mg/kg body weight/day of the inhibitor can be administered to a patient receiving these compositions. It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided dispersion in the composition will also depend upon the particular compound in the composition. In one aspect, the dosage amount of rifaximin in a provided composition is 40 mg. In another aspect, the dosage amount of rifaximin in a provided composition is 80 mg.

EXEMPLIFICATION

General Preparation of Solid Dispersions

The solid dispersions described herein can be prepared by a number of methods, including by melting and solvent evaporation. The solid dispersions of the present invention can also be prepared according to the procedures described in: Chiou W L, Riegelman S: "Pharmaceutical applications of solid dispersion systems", *J. Pharm. Sci.* 1971; 60: 1281-1302; Serajuddin ATM: "Solid dispersion of poorly water-soluble drugs: early promises, subsequent problems, and recent breakthroughs", J. Pharm. Sci. 1999; 88: 1058-1066; Leuner C, Dressman J: "Improving drug solubility for oral delivery using solid dispersions", *Eur. J. Pharm. Biopharm.* 2000; 50:47-60; and Vasconcelos T, Sarmento B, Costa P: "Solid dispersions as strategy to improve oral bioavailability of poor water soluble drugs", *Drug Discovery Today* 2007; 12:1068-1075, all of which are incorporated herein by reference in their entireties.

In one aspect, the components, e.g., rifaximin, polymer and methanol are mixed and then spray dried. Exemplary conditions are summarized in Table 1 below.

Exemplary Spray Drying Process Parameters, include for example:

Spray Dryer—e.g., PSD 1;

Single or multi-fluid nozzle: e.g., a two Fluid Niro Nozzle;

Nozzle orifice—0.1-10 mm;

Inlet gas temperature—75-150±5 deg C.;

Process gas flow (mmH2O)—20-70, preferred 44;

Atomizing gas pressure—0.7-1 bar;

Feed rate—2-7 kg/Hr;

Outlet temperature—30-70±3 deg C.;

Solution temperature—20-50 deg C.; and

Post spray drying vacuum dry at 20-60 deg C., for between about 2 and 72 hrs.

TABLE 1

| Description | Inlet temp. (set, °C.) (a) | Aspirator % | Pump % | Inlet temp. (measured, °C.) | Outlet temp. (measured, °C.) | Spray rate (b) mL/min |
|---|---|---|---|---|---|---|
| (50:50) HPMC-AS:rifaximin, ~10 g scale | 120 | 95 | 40-30 | 120-119 | 60-45 | 9.6 |

(a): approximate ratio of rifaximin to HPMC-AS, by weight.

(b): flow rates are estimated at 30% pump.

A representative batch formula is provided in Table 2.

TABLE 2

| Ingredient | Function | % w/w | Theoretical Quantity (kg/batch) |
|---|---|---|---|
| Rifaximin | Active | 47.20 | 22.18 |
| HPMC-AS | Polymer | 47.20 | 22.18 |
| Poloxamer 407 | Surfactant | 5.60 | 2.64 |
| Methanol[a] | Solvent | — | (438.0) |
| Nitrogen[b] | Process gas | — | — |
| Total Theoretical Weight | | 100.00 | 47.00 |

[a]Removed during drying process;

[b]Process gas for drying and atomization; not incorporated in product

Blending/Encapsulation Procedure

The components and composition of an 80 mg and 40 mg immediate and sustained extended release tables are proved in Table 3 below.

TABLE 3

| Ingredient | Function | Theoretical Quantity (mg/tablet) | | | |
|---|---|---|---|---|---|
| | | 80 mg-IR | 80 mg-SER | 40 mg-IR | 80 mg-IR |
| Rifaximin | Active | 80 | 80 | 40 | 40 |
| HPMC-AS | Polymer | 80 | 80 | 40 | 40 |
| Poloxamer 407 | Surfactant | 9.49 | 9.49 | 4.75 | 4.75 |
| Croscarmellose sodium | Dissolution enhancer | 30.15 | 11.33 | 20.74 | 11.33 |
| Microcrystalline cellulose | Filler | 25.28 | 44.10 | 119.43 | 128.84 |
| Colloidal silicon dioxide | Glidant | 0.45 | 0.45 | 0.45 | 0.45 |
| Magnesium stearate (non-bovine) | Lubricant | 1.13 | 1.13 | 1.13 | 1.13 |
| Opadry II Blue 85F90614 (PVA coating) | Coating | 11.92 | 11.92 | 11.92 | 11.92 |
| Purified Water | Solvent for Coating solution | — | — | — | — |
| Total Theoretical Weight | | 238.42 | 238.42 | 238.42 | 238.42 |

Clinical Data

The following data was obtained using the compositions described in Table 3.

A Phase 2, randomized, double-blind, placebo-controlled, parallel multicenter study evaluation of the efficacy (prevention of hospitalization for complications of liver cirrhosis or all-cause mortality in subjects with early decompensation) and safety of rifaximin SSD tablets in subjects with early decompensated liver cirrhosis was conducted. Subjects with documented ascites who had not previously experienced SBP, EVB, or HRS were enrolled in the study. Subjects completed a 1 to 21-day Screening Period, a 24-week Treatment Period, and a 2-week Follow-up Period. Approximately 420 subjects who successfully completed the Screening Period were randomized in a 1:1:1:1:1:1 allocation to 1 of 6 treatment groups and entered the Treatment Period. All treatments were administered once daily at bedtime. Assessments of efficacy and safety were performed during clinic visits at Day 1 (baseline), Weeks 2, 4, 8, 12, 16, 20, and 24 (End of Treatment [EOT]). All subjects completed an End of Study (EOS) visit at Week 26 (or early termination if applicable) for final safety assessments.

Inclusion Criteria

A subject was eligible for inclusion in this study if he/she met all of the following criteria:
1. Subject was ≥18 years of age.
2. Subject was male or female.

Females of childbearing (reproductive) potential had to have a negative serum pregnancy test at Screening and had to agree to use an acceptable method of contraception throughout their participation in the study. Acceptable methods of contraception included double barrier methods (condom with spermicidal jelly or a diaphragm with spermicide), hormonal methods (eg, oral contraceptives, patches or medroxyprogesterone acetate), or an intrauterine device (IUD) with a documented failure rate of less than 1% per year. Abstinence or partner(s) with a vasectomy could be considered an acceptable method of contraception at the discretion of the investigator. Note: Females who had been surgically sterilized (eg, hysterectomy or bilateral tubal ligation) or who were postmenopausal (total cessation of menses for >1 year) were not considered "females of childbearing potential."
3. Subject had a diagnosis of liver cirrhosis and documented ascites, either by imaging study or physical exam (Note: Subjects with Grade 1 ascites were permitted in the study), but had not yet experienced any of the following complications of cirrhosis:
   EVB—clinically significant gastrointestinal bleed
   SBP—greater than 250 polymorphonuclear (PMN) cells/$mm^3$ and/or positive monomicrobial culture in the ascitic fluid
   Renal failure in the presence of ascites—rise in the serum creatinine by 0.5 mg/dL (to greater than 1.5 mg/dL), with ascites documented on physical examination, imaging, and/or admitted on diuretics for the treatment of ascites
   Development of medically refractory ascites.
4. Subject had a MELD score of ≥12, a MELDNa score of ≥12, or a Child-Pugh B Classification (score=7-9).
5. Subject was capable of understanding the requirements of the study, and was willing to comply with all study procedures.
6. Subject understood the language of the informed consent form, and was capable and willing to sign the informed consent form.
7. If applicable, subject had a close family member or other personal contact that could provide continuing oversight to the subject and was available to the subject during the conduct of the trial.

Exclusion Criteria

A subject was not eligible for inclusion in this study if any of the following criteria applied:
1. Subject had a history of a major psychiatric disorder, including uncontrolled major depression or controlled or uncontrolled psychoses within the past 24 months prior to signing the informed consent (Diagnostic and Statistical Manual of Mental Disorders, 4th.) that, in the opinion of the investigator, would prevent completion of the study, interfere with analysis of study results, or negatively impact the subject's participation in the study.
2. Subject had history of alcohol abuse or substance abuse within the past 3 months prior to signing the informed consent (Diagnostic and Statistical Manual of Mental Disorders, 4th.).

3. Subject had documented primary sclerosing cholangitis (Note: subjects with primary biliary cirrhosis were allowed in the study).
4. Subject had undergone prophylactic variceal banding within 2 weeks of Screening or was scheduled to undergo prophylactic variceal banding during the study (Note: subjects with previous prophylactic variceal banding were allowed to participate in the study).
5. Subject had been diagnosed with an infection for which they are currently taking oral or parenteral antibiotics.
6. Subject had significant hypovolemia, or any electrolyte abnormality that could affect mental function (eg, serum sodium <125 mEq/L, serum calcium >10 mg/dL).
7. Subject had severe hypokalemia as defined by a serum potassium concentration <2.5 mEq/L.
8. Subject was anemic, as defined by a hemoglobin concentration of ≤8 g/dL.
9. Subject had renal insufficiency with a creatinine of ≥1.5 mg/dL.
   Note: Laboratory tests related to Inclusion/Exclusion criteria could be repeated once, before considering subject as a Screening Failure (given all other Inclusion/Exclusion criteria are met/not met respectively) at the discretion of the Investigator.
10. Subject showed presence of intestinal obstruction or has inflammatory bowel disease.
11. Subject had Type 1 or Type 2 diabetes that was poorly controlled in the opinion of the investigator or had had an HbA1c>12% within the past 3 months prior to Screening or at the Screening visit.
12. Subject had a history of seizure disorders.
13. Subject had unstable cardiovascular or pulmonary disease, categorized by a worsening in the disease condition that required a change in treatment or medical care within 30 days of randomization.
14. Subject had an active malignancy within the last 5 years (exceptions: basal cell carcinomas of the skin, or if female, in situ cervical carcinoma that had been surgically excised).
15. Subject had hepatocellular carcinoma (HCC). Note: Alpha-fetoprotein (AFP) concentration was measured at Screening. If the AFP was greater than 200 ng/mL, the subject was excluded from participation in the study. If the AFP was above the upper limit of normal and ≤200 ng/mL, cross-sectional imaging or ultrasonography techniques had to be used to rule out HCC.
16. Subject had any condition or circumstance that adversely affected the subject or could cause noncompliance with treatment or visits, could affect the interpretation of clinical data, or could otherwise contraindicate the subject's participation in the study.
17. If female, subject was pregnant or at risk of pregnancy, or was lactating.
18. Known varicella, herpes zoster, or other severe viral infection within 6 weeks of randomization.
19. Known human immunodeficiency virus (HIV) infection.
20. Subject had a positive stool test for *Yersinia enterocolitica, Campylobacter jejuni, Salmonella, Shigella*, ovum and parasites, and/or *Clostridium difficile*.
NOTE: Results of stool tests had to be confirmed as negative prior to randomization.
21. Subject had a history of tuberculosis infection and/or had received treatment for a tuberculosis infection. If subject had a previous positive skin test for tuberculosis antigen then they were to have a current negative chest X-ray to be eligible and could not have received previous treatment.
22. Subject was an employee of the site that was directly involved in the management, administration, or support of this study or was an immediate family member of the same.
23. Subject had a history of hypersensitivity to rifaximin, rifampin, rifamycin antimicrobial agents, or any of the components of rifaximin SSD.
24. Subject used any investigational product or device, or participated in another research study within 30 days prior to randomization.
25. Subject had a documented overt HE episode (Conn score ≥2) that had not resolved within 30 days of Visit 1 (Screening).

Treatments Administered

There were 6 treatment groups as listed below. The compositional components are presented above in Table 3. All treatments were to be administered orally qhs (at every bedtime). The duration of the treatment was 24 weeks.
Treatment A: rifaximin SSD 40 mg qhs (IR (immediate release) tablet)
Treatment B: rifaximin SSD 80 mg qhs (IR tablet)
Treatment C: rifaximin SSD 40 mg qhs (SER (sustained extended release) tablet)
Treatment D: rifaximin SSD 80 mg qhs (SER tablet)
Treatment E: rifaximin SSD 80 mg qhs (IR tablet)+ rifaximin 80 mg qhs (SER tablet)
Treatment F: Placebo qhs Primary Efficacy Endpoints Over the 24-week treatment period, the primary efficacy endpoint for the study was time to:
All-cause mortality, or
Hospitalization that was associated with 1 of the following complications of liver disease:
  HE—altered mental status diagnosed as HE, and defined as an increase of the Conn score to Grade ≥2 (ie, 0 or 1 to ≥2).
  EVB—occurrence of a clinically significant gastrointestinal bleed was defined as:
    Bleeding from an esophageal or gastric varix at the time of endoscopy, or
    The presence of large varices with blood evident in the stomach, and no other identifiable cause of bleeding observed during endoscopy.
    In addition, 1 or more of the following criteria had to be present:
      Drop in hemoglobin of greater than 2 g/dL over the first 48 hours post hospital admission,
      Transfusion requirement of 2 units of blood or more within 24 hours of hospital admission,
      A systolic blood pressure of less than 100 mm Hg, or
      Pulse rate greater than 100 beat/min at the time of admission.
Note: Baveno IV criteria was also used to further define variceal bleeding episodes.
  SBP—greater than 250 PMNcells/mm$^3$ and/or positive monomicrobial culture in the ascitic fluid.
  HRS was defined as:
    Progressive rise in serum creatinine (>1.5 mg/dL) with no improvement after at least 2 days with diuretic withdrawal and volume expansion with albumin;

Absence of parenchymal kidney disease;
Oliguria;
Absence of shock; and
No current or recent (within 3 months prior randomization) treatment with nephrotoxic drugs.

Key Secondary Efficacy Endpoints

The key secondary efficacy endpoints of this study were overall hospitalization rate for each of the individual component of the primary endpoint or all-cause mortality over the 24-week treatment period.

Other Secondary Endpoints

Other secondary endpoints of this study were the following:
Time to first hospitalization or all-cause mortality for each individual component of the primary endpoint.
All-cause hospitalization rate over the 24-week Treatment Period.
Liver cirrhosis mortality over the 24-week Treatment Period.
Time to development of medically refractory ascites, defined as ascites which could either no longer be effectively managed by:
A low sodium diet and maximal doses of diuretics (up to 400 mg spironolactone and 160 mg furosemide per day), or
Diuretics, due to the inability to tolerate side effects of maximal doses of diuretics.
Hospitalizations over the 24-week treatment period for all other infections.
Hospitalization as the result of Acute Kidney Injury (AKI) that was not attributable to HRS and was defined by a rapid reduction (over less than 48 hours) of kidney function as evidenced by:
A rise in serum creatinine, (with either an absolute increase in serum creatinine of ≥0.3 mg/dL (≥26.4 µmol/L) or percentage increase in serum creatinine of ≥50%), and
A reduction in urine output (defined as <0.5 ml/kg/hr for more than 6 hours).
Change in indices of Health Outcomes (Chronic Liver Disease Questionnaire (CLDQ_, Gastrointestinal Symptom Rating Scale (GSRS), Caregiver Burden Inventory (CBI), Epworth Sleepiness Scale (ESS)) at Weeks 4, 8, 12, 16, 20 and 24.
Pharmacokinetics of rifaximin and 25-desacetyl rifaximin assessing effects on factors including hepatic impairment, renal impairment and concomitant medications.
The critical flicker frequency (CFF) was assessed for each subject. CFF was assessed using a specialized CFF instrument.
Changes from baseline in blood ammonia concentrations at Weeks 2, 4, 8, 12, 16, 20 and 24.
Change from baseline in MELD (Model for End-Stage Liver Disease) and MELDNa (model end stage liver disease sodium) score at Weeks 2, 4, 8, 12, 16, 20 and 24.
Change from baseline in Child-Pugh score at Weeks 2, 4, 8, 12, 16, 20 and 24.

Drug Concentration Measurements

Rifaximin and metabolite concentration data was collected according to the Full Population PK Sampling design recommended in the FDA Guidance for Industry: Population Pharmacokinetics.

Disposition of Subjects

A total of 518 subjects were randomized in the study, of which 408 (78.8%) completed the study:
64 subjects in the 40 mg qhs IR group,
63 subjects in the 80 mg qhs IR group,
68 subjects in the 40 mg qhs SER group,
68 subjects in the 40 mg qhs SER group, 7
2 subjects in the 80 mg qhs SER group,
66 subjects in the combined IR/SER group and
75 subjects in the placebo group.

In total, 109 (21.0%) subjects prematurely discontinued from the study, with the largest number of discontinuations observed in the 80 mg qhs IR group (30.4%). The most common reason of premature discontinuation reported in the study was "withdrawal by subject"; this accounted for the premature discontinuation of 44 (8.5%) of all subjects that were randomized. This was followed by "death" which accounted for the premature discontinuation of 21 (4.1%) of all randomized subjects. Of all treatment groups, the 80 mg qhs IR group experienced the most number of premature discontinuations from the study (28 subjects in total), with "withdrawal by subject" reported as the most common reason of premature discontinuation (n=9).

Data Sets Analyzed

Two datasets were analyzed: ITT population and PP populations.
ITT population was defined as all randomized subjects who took at least 1 dose of study drug.
PP population was defined as all subjects in the ITT population with the exception of those who failed to meet inclusion criteria 3 or 4, or meet exclusion criterion 1.
Safety population included all randomized subjects who took at least 1 dose of study drug.
The analyses of baseline characteristics and efficacy were performed on the ITT population. The primary efficacy analyses were also performed on the PP population as a sensitivity analysis.

Analysis of Efficacy

The primary efficacy endpoint was the time to all-cause mortality or hospitalization that was associated with 1 of the following complications of liver disease: HE, EVB, SBP, or HRS over the 24-week treatment period was performed on the ITT population.

The primary analysis of time to hospitalization for any of the liver cirrhosis complications or all-cause mortality specified for the primary endpoint utilized a log-rank test stratified by analysis region (2-sided test at a significance level of 0.05).

Pairwise treatment group comparisons (each of the rifaximin SSD groups versus placebo) utilizing the log-rank test was also performed.

Additionally, Kaplan-Meier methods were used to estimate the proportion of subjects experiencing hospitalization for any of the liver cirrhosis complications or all-cause mortality on Days 28, 56, 84, 112, 140, and 168 for each treatment group.

Other analyses of the primary efficacy endpoint include sensitivity analyses (primary efficacy endpoint analyses using PP population) and prespecified subgroup analyses.

Time to Hospitalization for any of the Liver Cirrhosis Complications or all-Cause Mortality The primary efficacy endpoint was the time to all-cause mortality or hospitalization that was associated with 1 of the following complications of liver disease: HE, EVB, SBP, or HRS over the 24-week treatment period. Subjects who terminated early for reasons other than death were contacted approximately 24 weeks from randomization to determine if they experienced the primary endpoint. In the case of a subject's death, the subject's caregiver (if applicable) was contacted.

The time to hospitalization for any of the liver cirrhosis complications or all-cause mortality was defined as the duration between the date of first dose of the study drug and the date of first hospitalization for any of the liver cirrhosis complications or all-cause mortality.

Subjects who completed the entire 24-week treatment period without death or meeting the definition of liver cirrhosis complications of HE, EVB, SBP, or HRS were censored at the date of final visit (date of last contact). Subjects who prematurely discontinued before the end of the 24-week treatment period for reasons other than death were contacted monthly via a follow-up phone call for capture of cirrhosis complications, hospitalization, or death information. Subjects who did not meet the primary endpoint were censored at the date of last contact.

Primary Efficacy Analysis

Figure 2:
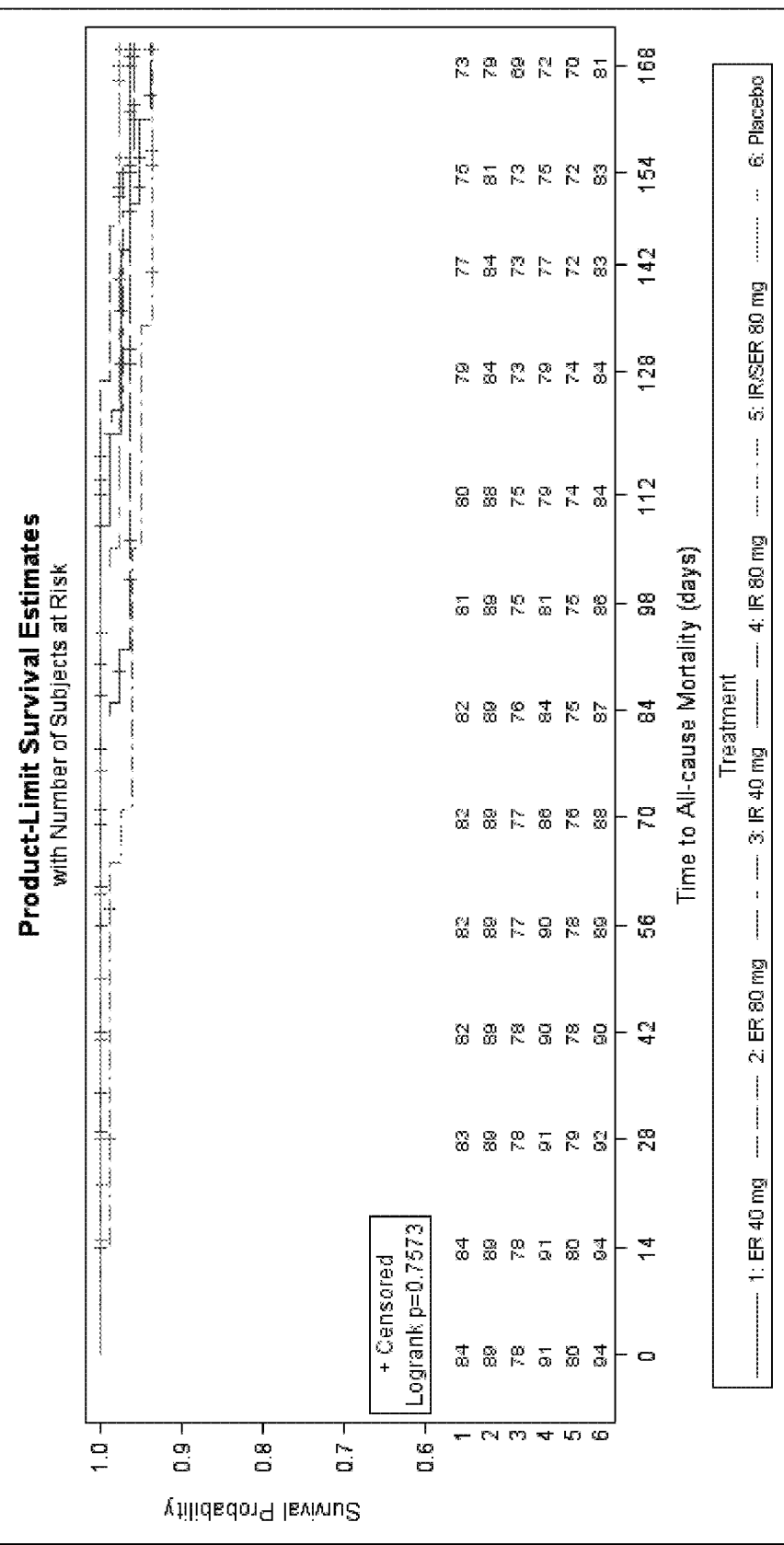
FIG. 2 presents a Kaplan-Meier estimate for the distribution of time to all-cause mortality by treatment group for an ITT population with a formulation comprising rifaximin solid dispersion.
Figure 3:
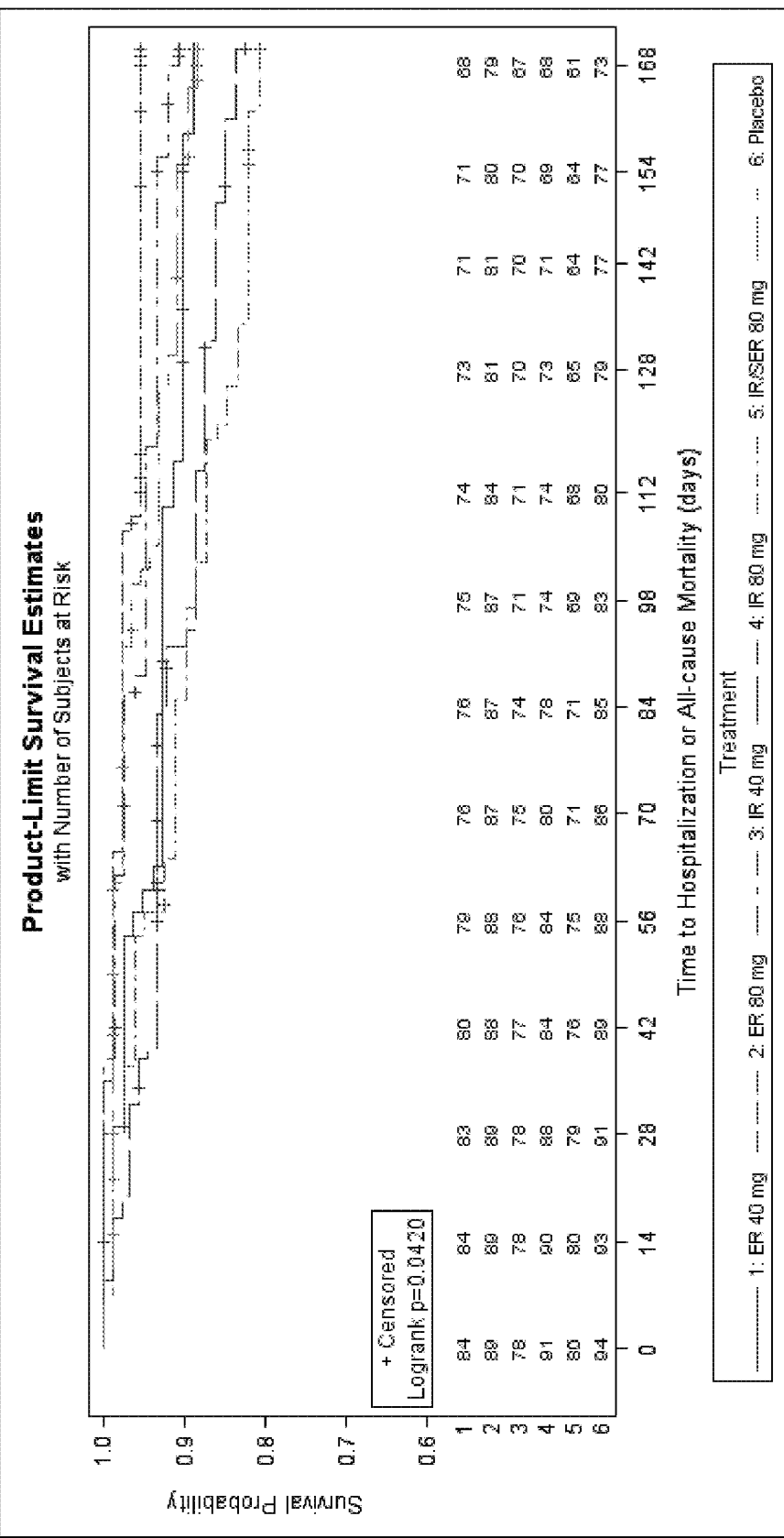
FIG. 3 presents a Kaplan-Meier estimate for the distribution of time to hospitalization for any of the liver cirrhosis complications or all-cause mortality by treatment group for the ITT population with a formulation comprising rifaximin solid dispersion.

The primary analysis did not demonstrate an overall statistically significant difference in time to hospitalization for any of the liver cirrhosis complications or all-cause mortality up to 24 weeks in any group. The overall treatment comparison effect for any of the rifaximin SSD treatments versus placebo was not statistically significant (stratified log-rank p=0.8062) (Table 4). FIG. 1 presents a Kaplan-Meier estimate for the distribution of time to hospitalization for any of the liver cirrhosis complications by treatment group for the ITT population. Based on the Kaplan-Meier estimates, the SER 80 mg qhs treatment group presented with the highest survival rate of all treatment groups and the combined IR/SER treatment group had the lowest survival rate; however this effect was not statistically significant (log-rank p=0.2262). FIG. 2 presents a Kaplan-Meier estimate for the distribution of time to all-cause mortality by treatment group for the ITT population. Based on the Kaplan-Meier estimates, the placebo group presented with the highest survival rate followed by the SER 80 mg qhs treatment group and the combined IR/SER treatment group had the lowest survival rate; however this effect was not statistically significant (log-rank p=0.7573). FIG. 3 presents a Kaplan-Meier estimate for the distribution of time to hospitalization for any of the liver cirrhosis complications or all-cause mortality by treatment group for the ITT population. Based on the Kaplan-Meier estimates, the SER 80 mg qhs treatment group presented with the highest survival rate and the combined IR/SER treatment group had the lowest survival rate; this effect was statistically significant (log-rank p=0.0420).

Supportive Analysis Based on the PP Population

Figure 4:
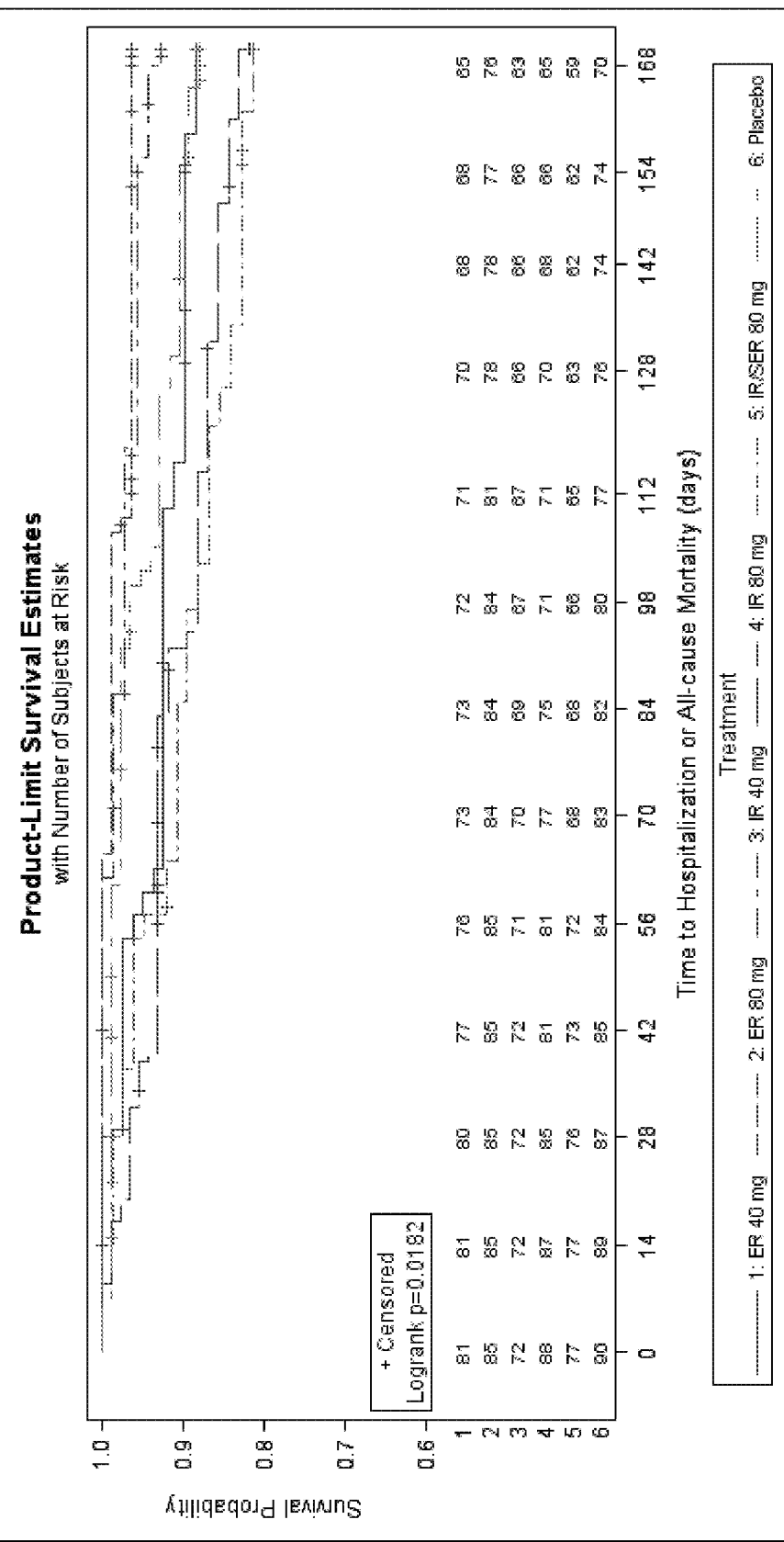
FIG. 4 presents a Kaplan-Meier estimate for the distribution of time to hospitalization for any of the liver cirrhosis complications or all-cause mortality by treatment group for the PP (per protocol) population with a formulation comprising rifaximin solid dispersion.

The results on the primary efficacy analysis based on the PP population were not consistent with the pairwise comparisons based on the ITT population (Table 4). The primary analysis on the PP population demonstrated a statistically significant difference in the time to hospitalization for any of the liver cirrhosis complications or all-cause mortality up to 24 weeks that was in favor of the SER 80 mg qhs treatment group versus placebo (stratified log-rank p=0.0464). There were no other statistically significant pairwise comparisons observed between the remaining active treatment groups and placebo (Table 5). The overall treatment comparison effect for any of the rifaximin SSD treatments versus placebo was not statistically significant (stratified log-rank p=0.9879). FIG. 4 presents a Kaplan-Meier estimate for the distribution of time to hospitalization for any of the liver cirrhosis complications or all-cause mortality by treatment group for the PP population. Based on the Kaplan-Meier estimates, the SER 80 mg qhs treatment group presented with the highest survival rate and the combined IR/SER treatment group had the lowest survival rate; this effect was statistically significant (log-rank p=0.0182).

TABLE 4

Time to Hospitalization for any of the Liver Cirrhosis Complications or All-cause Mortality up to 24 Weeks-ITT Population

| | # of Subjects | # of Events | Censored <Week 24 | Censored Week 24[1] | p-value[2] |
|---|---|---|---|---|---|
| Overall Treatment Comparison[3] | | | | | |
| Any Rifaximin SSD Treatment | 422 | 50 (11.8%) | 31 (7.3%) | 341 (80.8%) | 0.8062 |
| Placebo | 94 | 10 (10.6%) | 11 (11.7%) | 73 (77.7%) | |
| Pairwise Comparisons (versus Placebo)[3] | | | | | |
| Treatment A: Rifaximin SSD 40 mg qhs (IR Tablet) | 78 | 7 (9.0%) | 5 (6.4%) | 66 (84.6%) | 0.6316 |
| Treatment B: Rifaximin SSD 80 mg qhs (IR Tablet) | 91 | 15 (16.5%) | 9 (9.9%) | 67 (73.6%) | 0.2283 |
| Treatment C: Rifaximin SSD 40 mg qhs (SER Tablet) | 84 | 9 (10.7%) | 7 (8.3%) | 68 (81.0%) | 0.9666 |
| Treatment D: Rifaximin SSD 80 mg qhs (SER Tablet) | 89 | 4 (4.5%) | 6 (6.7%) | 79 (88.8%) | 0.0991 |

TABLE 4-continued

Time to Hospitalization for any of the Liver Cirrhosis
Complications or All-cause Mortality up to 24 Weeks-ITT Population

| | # of Subjects | # of Events | Censored <Week 24 | Censored Week 24[1] | p-value[2] |
|---|---|---|---|---|---|
| Treatment E: Rifaximin SSD 80 mg qhs (IR Tablet) and Rifaximin SSD 80 mg qhs (SER Tablet) | 80 | 15 (18.8%) | 4 (5.0%) | 61 (76.3%) | 0.1792 |

IR = immediate release;
ITT = intent to treat;
qhs = once daily at bedtime;
SER = sustained extended release;
SSD = solid soluble dispersion.
[1]Number of subjects censored at Week 24 (subject did not experience an event and was enrolled in the study at Week 24).
[2]P-value was obtained using a stratified log-rank test.
[3]Stratified by analysis region (study centers are grouped within 2 regions, centers in the United States and centers in Russia)

TABLE 5

Time to Hospitalization for any of the Liver Cirrhosis
Complications or All-cause Mortality up to 24 Weeks-PP Population

| | # of Subjects | # of Events | Censored <Week 24 | Censored Week 24[2] | p-value[3] |
|---|---|---|---|---|---|
| Overall Treatment Comparison[4] | | | | | |
| Any Rifaximin SSD Treatment | 403 | 46 (11.4%) | 31 (7.7%) | 326 (80.9%) | 0.9879 |
| Placebo | 90 | 10 (11.1%) | 10 (11.1%) | 70 (77.8%) | |
| Pairwise Comparisons (versus Placebo)[4] | | | | | |
| Treatment A: Rifaximin SSD 40 mg qhs (IR Tablet) | 72 | 5 (6.9%) | 5 (6.9%) | 62 (86.1%) | 0.3116 |
| Treatment B: Rifaximin SSD 80 mg qhs (IR Tablet) | 88 | 15 (17.0%) | 9 (10.2%) | 64 (72.7%) | 0.2247 |
| Treatment C: Rifaximin SSD 40 mg qhs (SER Tablet) | 81 | 9 (11.1%) | 7 (8.6%) | 65 (80.2%) | 0.9641 |
| Treatment D: Rifaximin SSD 80 mg qhs (SER Tablet) | 85 | 3 (3.5%) | 6 (7.1%) | 76 (89.4%) | 0.0464 |
| Treatment E: Rifaximin SSD 80 mg qhs (IR Tablet) and Rifaximin SSD 80 mg qhs (SER Tablet) | 77 | 14 (18.2%) | 4 (5.2%) | 59 (76.6%) | 0.2523 |

IR = immediate release;
ITT = intent to treat;
PP = per protocol;
qhs = once daily at bedtime;
SER = sustained extended release;
SSD = solid soluble dispersion.
[1]All subjects in the ITT population except those that failed inclusion criteria 3, 4 or met exclusion criterion 1.
[2]Number of subjects censored at Week 24 (subject did not experience an event and was enrolled in the study at Week 24.
[3]P-value was obtained using a stratified log-rank test.
[4]Stratified by analysis region (study centers are grouped within 2 regions, centers in the United States and centers in Russia).

Prespecified Subgroup Analyses of the Primary Efficacy Endpoint

Baseline MELD Category

The influence of a subject's baseline MELD category on the primary efficacy analysis was evaluated. Baseline MELD subgroups were categorized as MELD scores of ≤10, 11 to 18, 19 to 24, or ≥25. None of the pairwise comparisons versus placebo were statistically significant in any of the subgroups. The overall treatment comparison effect for any of the rifaximin SSD treatment versus placebo was not statistically significant (MELD score of ≤10: stratified log-rank p=0.8486; MELD score: 11 to 18 stratified log-rank p=0.7937; MELD score of 19 to 24: stratified log-rank p=0.3154; and MELD score of ≥25: stratified log-rank p=not applicable [1 event out of 1 subject]).

Baseline MELDNa Category

The influence of a subject's baseline MELDNa category on the primary efficacy analysis was evaluated. Baseline MELDNa subgroups were categorized as MELDNa scores of ≤10, 11 to 18, 19 to 24, or ≥25. None of the pairwise comparisons versus placebo were statistically significant in any of the subgroups. The overall treatment comparison effect for any of the rifaximin SSD treatment versus placebo was not statistically significant (MELDNa score of ≤10: stratified log-rank p=0.3200; MELDNa score: 11 to 18 stratified log-rank p=0.9368; MELDNa score of 19 to 24:

stratified log-rank p=0.2608; and MELDNa score of ≥25: stratified log-rank p=not applicable (3 events out of 4 subjects)).

Baseline Child-Pugh Classification

The influence of a subject's baseline Child-Pugh classification on the primary efficacy analysis was evaluated. The baseline Child-Pugh classification subgroups were categorized as Class A, Class B, or Class C. None of the pairwise treatment comparisons versus placebo were statistically significant in any of the subgroups. The overall treatment comparison effect for any of the rifaximin SSD treatments versus placebo was not statistically significant (Class A: stratified log-rank p=not applicable (zero events); Class B: stratified log-rank p=0.7942 and Class C: stratified log-rank p=0.9516).

Baseline Conn Score

The influence of a subject's baseline Conn score on the primary efficacy analysis was evaluated. Baseline Conn score subgroups were categorized as 0, 1, or 2. Table 6 presents the analysis of the primary efficacy endpoint by baseline Conn score. Consistent with the results of the PP population, a statistically significant difference in the time to hospitalization for any of the liver cirrhosis complications or all-cause mortality was observed within the Conn score subgroup 0 and was in favor of the SER 80 mg qhs treatment group versus placebo (stratified log-rank p=0.0460). This statistical significance was not evident within the Conn score subgroups 1 or 2 (although, subgroup 2 had 1 event out of 2 subjects).

The overall treatment comparison effect for any of the rifaximin SSD treatments versus placebo was not statistically significant for any subgroup (Conn score 0: stratified log-rank p=0.8915; Conn score 1: stratified log-rank p=0.8251; Conn score 2: not applicable [1 event out of 2 subjects]).

TABLE 6

Analysis of Primary Efficacy Endpoint: Time to Hospitalization for any of the Liver Cirrhosis Complications or All-cause Mortality by Baseline Conn Score up to 24 Weeks (Day 170)-ITT Population

| | # of Subjects | # of Events | Censored | | p-value[2] |
| --- | --- | --- | --- | --- | --- |
| | | | <Week 24 | Week 24[1] | |
| Conn Score: 0 | | | | | |
| Overall Treatment Comparison[3] | | | | | |
| Any Rifaximin SSD Treatment | 260 | 34 (13.1%) | 20 (7.7%) | 206 (79.2%) | 0.8915 |
| Placebo | 57 | 7 (12.3%) | 6 (10.5%) | 44 (77.2%) | |
| Pairwise Comparisons (versus Placebo)[3] | | | | | |
| Treatment A: Rifaximin SSD 40 mg qhs (IR Tablet) | 48 | 7 (14.6%) | 3 (6.3%) | 38 (79.2%) | 0.7477 |
| Treatment B: Rifaximin SSD 80 mg qhs (IR Tablet) | 55 | 11 (20.0%) | 7 (12.7%) | 37 (67.3%) | 0.2297 |
| Treatment C: Rifaximin SSD 40 mg qhs (SER Tablet) | 53 | 4 (7.5%) | 5 (9.4%) | 44 (83.0%) | 0.4007 |
| Treatment D: Rifaximin SSD 80 mg qhs (SER Tablet) | 48 | 1 (2.1%) | 4 (8.3%) | 43 (89.6%) | 0.0460 |
| Treatment E: Rifaximin SSD 80 mg qhs (IR Tablet) and Rifaximin SSD 80 mg qhs (SER Tablet) | 56 | 11 (19.6%) | 1 (1.8%) | 44 (78.6%) | 0.3340 |
| Conn Score: 1 | | | | | |
| Overall Treatment Comparison[3] | | | | | |
| Any Rifaximin SSD Treatment | 160 | 15 (9.4%) | 11 (6.9%) | 134 (83.8%) | 0.8251 |
| Placebo | 37 | 3 (8.1%) | 5 (13.5%) | 29 (78.4%) | |
| Pairwise Comparisons (versus Placebo)[3] | | | | | |
| Treatment A: Rifaximin SSD 40 mg qhs (IR Tablet) | 30 | 0 | 2 (6.7%) | 28 (93.3%) | 0.0941 |
| Treatment B: Rifaximin SSD 80 mg qhs (IR Tablet) | 36 | 4 (11.1%) | 2 (5.6%) | 30 (83.3%) | 0.7015 |
| Pairwise Comparisons (versus Placebo)[3] | | | | | |
| Treatment C: Rifaximin SSD 40 mg qhs (SER Tablet) | 31 | 5 (16.1%) | 2 (6.5%) | 24 (77.4%) | 0.3467 |
| Treatment D: Rifaximin SSD 80 mg qhs (SER Tablet) | 39 | 2 (5.1%) | 2 (5.1%) | 35 (89.7%) | 0.5204 |

TABLE 6-continued

Analysis of Primary Efficacy Endpoint: Time to Hospitalization for any of the Liver Cirrhosis
Complications or All-cause Mortality by Baseline Conn Score up to 24 Weeks (Day 170)-ITT Population

|  | # of Subjects | # of Events | Censored <Week 24 | Censored Week 24[1] | p-value[2] |
|---|---|---|---|---|---|
| Treatment E: Rifaximin SSD 80 mg qhs (IR Tablet) and Rifaximin SSD 80 mg qhs (SER Tablet) | 24 | 4 (16.7%) | 3 (12.5%) | 17 (70.8%) | 0.3075 |
| Conn Score: 2 | | | | | |
| Overall Treatment Comparison[3] | | | | | |
| Any Rifaximin SSD Treatment | 2 | 1 (50.0%) | 0 | 1 (50.0%) | |
| Pairwise Comparisons (versus Placebo)[3] | | | | | |
| Treatment D: Rifaximin SSD 80 mg qhs (SER Tablet) | 2 | 1 (50.0%) | 0 | 1 (50.0%) | |

IR = immediate release;
ITT = intent to treat;
qhs = once daily at bedtime;
SER = sustained extended release;
SSD = solid soluble dispersion.
[1]Number of subjects censored at Week 24 (subject did not experience an event and was enrolled in the study at Week 24).
[2]P-value was obtained using a stratified log-rank test.
[3]Stratified by analysis region (study centers are grouped within 2 regions, centers in the United States and centers in Russia)

Time Since First Diagnosis of Liver Cirrhosis

The influence of a subject's time since first diagnosis of liver cirrhosis on the primary efficacy analysis was evaluated. The time since first diagnosis of liver cirrhosis subgroups were categorized as <947 days or ≥947 days. Table 7 presents the analysis of the primary efficacy endpoint by time since first diagnoses of liver cirrhosis. A near statistically significant difference in the time to hospitalization for any of the liver cirrhosis complications or all-cause mortality was observed within ≥947 days subgroup and, like the PP and baseline Conn score 0 populations, was in favor of the SER 80 mg qhs treatment group versus placebo (stratified log-rank p=0.0517). The overall treatment comparison effect for any of the rifaximin SSD treatment versus placebo was not statistically significant (time since first diagnosis of liver cirrhosis: <947 days stratified log-rank p=0.3961; time since first diagnosis of liver cirrhosis: ≥947 days stratified log-rank p=0.5689).

TABLE 7

Analysis of Primary Efficacy Endpoint: Time to Hospitalization
for any of the Liver Cirrhosis Complications or All-cause Mortality by Categorized
Time Since First Diagnosis of Liver Cirrhosis up to 24 Weeks (Day 170)-ITT Population

|  | # of Subjects | # of Events | Censored <Week 24 | Censored Week 24[1] | p-value[2] |
|---|---|---|---|---|---|
| <947 Days | | | | | |
| Overall Treatment Comparison[3] | | | | | |
| Any Rifaximin SSD Treatment | 206 | 32 (15.5%) | 14 (6.8%) | 160 (77.7%) | 0.3961 |
| Placebo | 50 | 5 (10.0%) | 7 (14.0%) | 38 (76.0%) | |
| Pairwise Comparisons (versus Placebo)[3] | | | | | |
| Treatment A: Rifaximin SSD 40 mg qhs (IR Tablet) | 43 | 3 (7.0%) | 3 (7.0%) | 37 (86.0%) | 0.4929 |
| Treatment B: Rifaximin SSD 80 mg qhs (IR Tablet) | 41 | 8 (19.5%) | 7 (17.1%) | 26 (63.4%) | 0.2329 |
| Treatment C: Rifaximin SSD 40 mg qhs (SER Tablet) | 46 | 8 (17.4%) | 2 (4.3%) | 36 (78.3%) | 0.3436 |
| Treatment D: Rifaximin SSD 80 mg qhs (SER Tablet) | 34 | 3 (8.8%) | 1 (2.9%) | 30 (88.2%) | 0.7582 |

TABLE 7-continued

Analysis of Primary Efficacy Endpoint: Time to Hospitalization
for any of the Liver Cirrhosis Complications or All-cause Mortality by Categorized
Time Since First Diagnosis of Liver Cirrhosis up to 24 Weeks (Day 170)-ITT Population

|  | # of Subjects | # of Events | Censored <Week 24 | Week 24[1] | p-value[2] |
|---|---|---|---|---|---|
| Treatment E: Rifaximin SSD 80 mg qhs (IR Tablet) and Rifaximin SSD 80 mg qhs (SER Tablet) | 42 | 10 (23.8%) | 1 (2.4%) | 31 (73.8%) | 0.1237 |

|  | Censored # of Subjects | # of Events | Censored # of Subjects | # of Events |
|---|---|---|---|---|
| | ≥947 Days | | | |
| Overall Treatment Comparison[3] | | | | |
| Any Rifaximin SSD Treatment | 215 | 18 (8.4%) | 16 (7.4%) | 181 (84.2%) 0.5689 |
| Placebo | 44 | 5 (11.4%) | 4 (9.1%) | 35 (79.5%) |
| Pairwise Comparisons (versus Placebo)[3] | | | | |
| Treatment A: Rifaximin SSD 40 mg qhs (IR Tablet) | 34 | 4 (11.8%) | 1 (2.9%) | 29 (85.3%) 0.9598 |
| Treatment B: Rifaximin SSD 80 mg qhs (IR Tablet) | 50 | 7 (14.0%) | 2 (4.0%) | 41 (82.0%) 0.6094 |
| Treatment C: Rifaximin SSD 40 mg qhs (SER Tablet) | 38 | 1 (2.6%) | 5 (13.2%) | 32 (84.2%) 0.1523 |
| Treatment D: Rifaximin SSD 80 mg qhs (SER Tablet) | 55 | 1 (1.8%) | 5 (9.1%) | 49 (89.1%) 0.0517 |
| Treatment E: Rifaximin SSD 80 mg qhs (IR Tablet) and Rifaximin SSD 80 mg qhs (SER Tablet) | 38 | 5 (13.2%) | 3 (7.9%) | 30 (78.9%) 0.8519 |

IR = immediate release;
ITT = intent to treat;
qhs = once daily at bedtime;
SER = sustained extended release;
SSD = solid soluble dispersion.
[1]Number of subjects censored at Week 24 (subject did not experience an event and was enrolled in the study at Week 24).
[2]P-value was obtained using a stratified log-rank test.
[3]Stratified by analysis region (study centers are grouped within 2 regions, centers in the United States and centers in Russia).

Time to Development of Medically Refractory Ascites up to Week 24 (Day 170)

Analysis of the time to development of medically refractory ascites up to Week 24 (Day 170) is presented in Table 8.

A statistically significant difference in time to development of medically refractory ascites up to 24 Week was observed in favor of the IR 40 mg qhs treatment group versus placebo (stratified log-rank p=0.0308) and in favor of the SER 40 mg qhs treatment group versus placebo (stratified log-rank p=0.0202). No other pairwise treatment comparisons versus placebo were statistically significant. The overall treatment comparison for any of the rifaximin SSD treatments versus placebo was not statistically significant.

TABLE 8

Analysis of Secondary Efficacy Endpoint: Time to Development
of Medically Refractory Ascites up to 24 Week (Day170)-ITT Population

|  | # of Subjects | # of Events | Censored <Week 24 | Week 24[1] | p-value[2] |
|---|---|---|---|---|---|
| Overall Treatment Comparison[3] | | | | | |
| Any Rifaximin SSD Treatment | 422 | 16 (3.8%) | 51 (12.1%) | 355 (84.1%) | 0.0601 |
| Placebo | 94 | 0 | 13 (13.8%) | 81 (86.2%) | |
| Pairwise Comparisons (versus Placebo)[3] | | | | | |
| Treatment A: Rifaximin SSD 40 mg qhs (Immediate Release [IR] Tablet) | 78 | 4 (5.1%) | 8 (10.3%) | 66 (84.6%) | 0.0308 |

TABLE 8-continued

Analysis of Secondary Efficacy Endpoint: Time to Development
of Medically Refractory Ascites up to 24 Week (Day170)-ITT Population

| | # of Subjects | # of Events | Censored <Week 24 | Censored Week 24[1] | p-value[2] |
|---|---|---|---|---|---|
| Treatment B: Rifaximin SSD 80 mg qhs (Immediate Release [IR] Tablet) | 91 | 3 (3.3%) | 18 (19.8%) | 70 (76.9%) | 0.0721 |
| Treatment C: Rifaximin SSD 40 mg qhs (Sustained Extended Release [SER] Tablet) | 84 | 5 (6.0%) | 9 (10.7%) | 70 (83.3%) | 0.0202 |
| Treatment D: Rifaximin SSD 80 mg qhs (Sustained Extended Release [SER] Tablet) | 89 | 2 (2.2%) | 8 (9.0%) | 79 (88.8%) | 0.1508 |
| Treatment E: Rifaximin SSD 80 mg qhs (IR Tablet) and Rifaximin SSD 80 mg qhs (SER Tablet) | 80 | 2 (2.5%) | 8 (10.0%) | 70 (87.5%) | 0.1319 |

IR = immediate release;
ITT = intent to treat;
qhs = once daily at bedtime;
SER = sustained extended release;
SSD = solid soluble dispersion.
[1]Number of subjects censored at Week 24 (subject did not experience an event and was enrolled in the study at Week 24).
[2]P-value was obtained using a stratified log-rank test.
[3]Stratified by analysis region (study centers are grouped within 2 regions, centers in the United States and centers in Russia).

Efficacy Conclusions

Based on Kaplan Meier estimates of distribution of time to hospitalization for any of the liver cirrhosis complications or all-cause mortality up to 24 weeks, there was a statistically significant effect in favor of the SER 80 mg qhs and combined IR/SER qhs treatment groups having the highest and lowest survival rates, respectively.

The primary analysis on the PP population did demonstrate a statistically significant difference in the time to hospitalization for any of the liver cirrhosis complications or all-cause mortality up to 24 weeks that was in favor of the SER 80 mg qhs treatment group versus placebo. Kaplan Meier estimates of distribution of time to hospitalization for any of the liver cirrhosis complications or all-cause mortality up to 24 weeks were also statistically significant in favor of the SER 80 mg qhs and combined IR/SER qhs treatment groups having the highest and lowest survival rates, respectively.

In the secondary analysis, there was a statistically significant difference in time to development of medical refractory ascites up to Week 24 in favor of the IR 40 mg qhs and SER 40 mg qhs treatment groups versus placebo. There was a statistically significant effect for change from baseline in ESS total score was statistically significant treatment versus placebo effect was observed at Week 4 at the 25th percentile for baseline (p<0.0001), with the IR 40 mg qhs treatment group presenting with the greatest decrease from baseline.

These studies show, for the primary analysis, overall time to hospitalization for any of the liver cirrhosis complications or all-cause mortality up to 24 weeks was in favor of the SER 80 mg qhs treatment group versus placebo. In the secondary analysis, statistically significant favorable effects were observed most consistently in the IR 40 mg qhs treatment group as well as occurrences in the combined IR/SER qhs and SER 40 mg qhs treatment groups.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A method of preventing complications of liver disease in a subject having liver cirrhosis, comprising administering to the subject an immediate release pharmaceutical composition comprising from about 16 wt % to about 18 wt % rifaximin and from about 16 wt % to about 18 wt % HPMC-AS, wherein the total amount of rifaximin is 40 mg and wherein the complications of liver disease are selected from the group consisting of hepatic encephalopathy (HE), esophageal variceal bleeding (EVB), spontaneous bacterial peritonitis (SBP), and hepatorenal syndrome (HRS).

2. The method of claim 1, wherein the composition is in the form of a tablet.

3. The method of claim 1, wherein the complication of liver disease is hepatic encephalopathy (HE).

4. The method of claim 1, wherein the complication of liver disease is esophageal variceal bleeding (EVB).

5. The method of claim 1, wherein the complication of liver disease is spontaneous bacterial peritonitis (SBP).

6. The method of claim 1, wherein the complication of liver disease is hepatorenal syndrome (HRS).

* * * * *